(12) United States Patent
Song et al.

(10) Patent No.: US 10,849,599 B2
(45) Date of Patent: Dec. 1, 2020

(54) METHOD AND APPARATUS FOR GENERATING BODY MARKER

(71) Applicant: SAMSUNG MEDISON CO., LTD., Hongcheon-gun (KR)

(72) Inventors: Min-jung Song, Hongcheon-gun (KR); Yoon-woo Jun, Seoul (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 829 days.

(21) Appl. No.: 14/753,139

(22) Filed: Jun. 29, 2015

(65) Prior Publication Data

US 2016/0174944 A1 Jun. 23, 2016

(30) Foreign Application Priority Data

Dec. 23, 2014 (KR) .................. 10-2014-0187502
Apr. 13, 2015 (KR) .................. 10-2015-0052077

(51) Int. Cl.
  *A61B 8/08* (2006.01)
  *A61B 8/00* (2006.01)
  *G06F 19/00* (2018.01)

(52) U.S. Cl.
  CPC .............. *A61B 8/5215* (2013.01); *A61B 8/08* (2013.01); *A61B 8/461* (2013.01); *A61B 8/465* (2013.01); *A61B 8/467* (2013.01); *A61B 8/468* (2013.01); *A61B 8/486* (2013.01); *A61B 8/488* (2013.01); *G06F 19/321* (2013.01); *A61B 8/4405* (2013.01); *A61B 8/4427* (2013.01); *A61B 8/565* (2013.01)

(58) Field of Classification Search
  CPC ....... A61B 8/5215; A61B 8/467; A61B 8/461; A61B 8/486; A61B 8/488; A61B 8/08; A61B 8/465; A61B 8/468; A61B 8/4405; A61B 8/4427; A61B 8/565; G06F 19/321
  See application file for complete search history.

(56) References Cited

U.S. PATENT DOCUMENTS

| | | | |
|---|---|---|---|
| 8,696,575 B2 | 4/2014 | Kamiyama et al. | |
| 2009/0076385 A1 | 3/2009 | Jackson et al. | |
| 2010/0189322 A1 | 7/2010 | Sakagawa | |
| 2014/0029832 A1* | 1/2014 | Molnar | G06T 7/194 382/132 |
| 2014/0088427 A1 | 3/2014 | Tashiro | |

(Continued)

FOREIGN PATENT DOCUMENTS

| | | |
|---|---|---|
| EP | 2 783 635 A1 | 10/2014 |
| JP | 2007-29456 A | 2/2007 |

(Continued)

OTHER PUBLICATIONS

Communication dated May 23, 2016 issued by the European Patent Office in counterpart European Patent Application No. 15169486.6.

*Primary Examiner* — Elmer M Chao
(74) *Attorney, Agent, or Firm* — Sughrue Mion, PLLC

(57) ABSTRACT

A method of generating a body marker includes detecting a portion corresponding to a shape of an object shown in a medical image from a first body marker by comparing the shape of the object with the first body marker, generating a second body marker in which the portion detected from the first body marker has been emphasized, and outputting the second body marker.

15 Claims, 37 Drawing Sheets

(56) References Cited

U.S. PATENT DOCUMENTS

2014/0296711 A1   10/2014   Lee
2014/0341449 A1   11/2014   Tizhoosh et al.

FOREIGN PATENT DOCUMENTS

| JP | 2007-313114 A | 12/2007 |
| JP | 2008-142330 A | 6/2008 |
| JP | 2014-64637 A | 4/2014 |

* cited by examiner

METHOD AND APPARATUS FOR GENERATING BODY MARKER

RELATED APPLICATION

This application claims the benefit of Korean Patent Applications No. 10-2014-0187502, filed on Dec. 23, 2014, and No. 10-2015-0052077, filed on Apr. 13, 2015, in the Korean Intellectual Property Office, the disclosure of which is incorporated herein in its entirety by reference.

BACKGROUND

1. Field

One or more exemplary embodiments relate to a method and apparatus for generating a body marker.

2. Description of the Related Art

Ultrasound diagnosis apparatuses transmit ultrasound signals generated by transducers of a probe to an object and receive echo signals reflected from the object, thereby obtaining at least one image of an internal part of the object (e.g., soft tissues or blood flow). In particular, ultrasound diagnosis apparatuses are used for medical purposes including observation of the interior of an object, detection of foreign substances, and diagnosis of damage to the object. Such ultrasound diagnosis apparatuses provide high stability, display images in real time, and are safe due to the lack of radioactive exposure compared to X-ray apparatuses. Therefore, ultrasound diagnosis apparatuses are widely used together with other image diagnosis apparatuses including a computed tomography (CT) apparatus, a magnetic resonance imaging (MRI) apparatus, and the like.

In general, a body marker added to an ultrasound image is determined when a user selects one from among previously generated body markers. Thus, it is difficult to determine an accurate position of an object shown in an ultrasound image via the body marker.

SUMMARY

One or more exemplary embodiments include a method and apparatus for generating a body marker.

One or more exemplary embodiments include a non-transitory computer-readable recording medium for storing a program for executing the method of generating a body marker.

Additional aspects will be set forth in part in the description which follows and, in part, will be apparent from the description, or may be learned by practice of the presented exemplary embodiments.

According to one or more exemplary embodiments, a method of generating a body marker includes: detecting a portion corresponding to a shape of an object shown in a medical image from a first body marker by comparing the shape of the object with the first body marker; generating a second body marker in which the portion detected from the first body marker has been emphasized; and outputting the second body marker.

In the method, each of the first and second body markers may include a two-dimensional (2D) or three-dimensional (3D) body marker.

The first body marker may include a body marker that is selected from among a plurality of prestored body markers according to a user input.

The method may further include segmenting the shape of the object from the medical image, and the first body marker may include a body marker that is selected from among a plurality of prestored body markers based on the segmented shape of the object.

The method may further include receiving a user input for designating one body marker from among the plurality of prestored body markers; and changing the selected body marker to the designated body marker.

In the generating of the second body marker, the second body marker may be generated by partitioning the first body marker into a plurality of portions and emphasizing a portion including the detected portion among the plurality of portions.

The first body marker may be partitioned into the plurality of portions that include the portion corresponding to the shape of the object shown in the medical image.

The first body marker may be partitioned into the plurality of portions according to prestored anatomical theory.

In the generating of the second body marker, the second body marker may be generated by indicating the portion detected from the first body marker as a line having a different thickness than that of a line depicting the first body marker.

In the generating of the second body marker, the second body marker may be generated by indicating the portion detected from the first body marker as a color that is different from a color representing the first body marker.

In the generating of the second body marker, the second body marker may be generated by indicating the detected portion as being larger than the remaining portions of the first body marker.

The medical image may include one selected from the group consisting of an amplitude (A) mode ultrasound image, a brightness (B) mode ultrasound image, a motion (M) mode ultrasound image, and a Doppler mode ultrasound image.

According to one or more exemplary embodiments, a non-transitory computer-readable recording medium has recorded thereon a program, which when executed by a computer, performs the above method.

According to one or more exemplary embodiments, an apparatus for generating a body marker includes: a controller configured to detect a portion corresponding to a shape of an object shown in a medical image from a first body marker by comparing the shape of the object with the first body marker and generate a second body marker in which the portion detected from the first body marker has been emphasized; and a display configured to output the second body marker.

Each of the first and second body markers may include a 2D or 3D body marker.

The first body marker may include a body marker that is selected from among a plurality of prestored body markers according to a user input.

The apparatus may further include an image processor configured to segment the shape of the object from the medical image, and the first body marker may include a body marker that is selected from among a plurality of prestored body markers based on the segmented shape of the object.

The apparatus may further include an input unit configured to receive a user input for designating one body marker from among the plurality of prestored body markers, and the controller may change the selected body marker to the designated body marker.

The controller may generate the second body marker by partitioning the first body marker into a plurality of portions and emphasizing a portion including the detected portion among the plurality of portions.

The first body marker may be partitioned into the plurality of portions that include the portion corresponding to the shape of the object shown in the medical image.

The first body marker may be partitioned into the plurality of portions according to prestored anatomical theory.

The controller may generate the second body marker by indicating the portion detected from the first body marker as a line having a different thickness than that of a line depicting the first body marker.

The controller may generate the second body marker by indicating the portion detected from the first body marker as a line having a different thickness than that of a line depicting the first body marker.

The controller may generate the second body marker by indicating the detected portion as being larger than the remaining portions of the first body marker.

The medical image may include one selected from the group consisting of an A mode ultrasound image, a B mode ultrasound image, an M mode ultrasound image, and a Doppler mode ultrasound image.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1B:
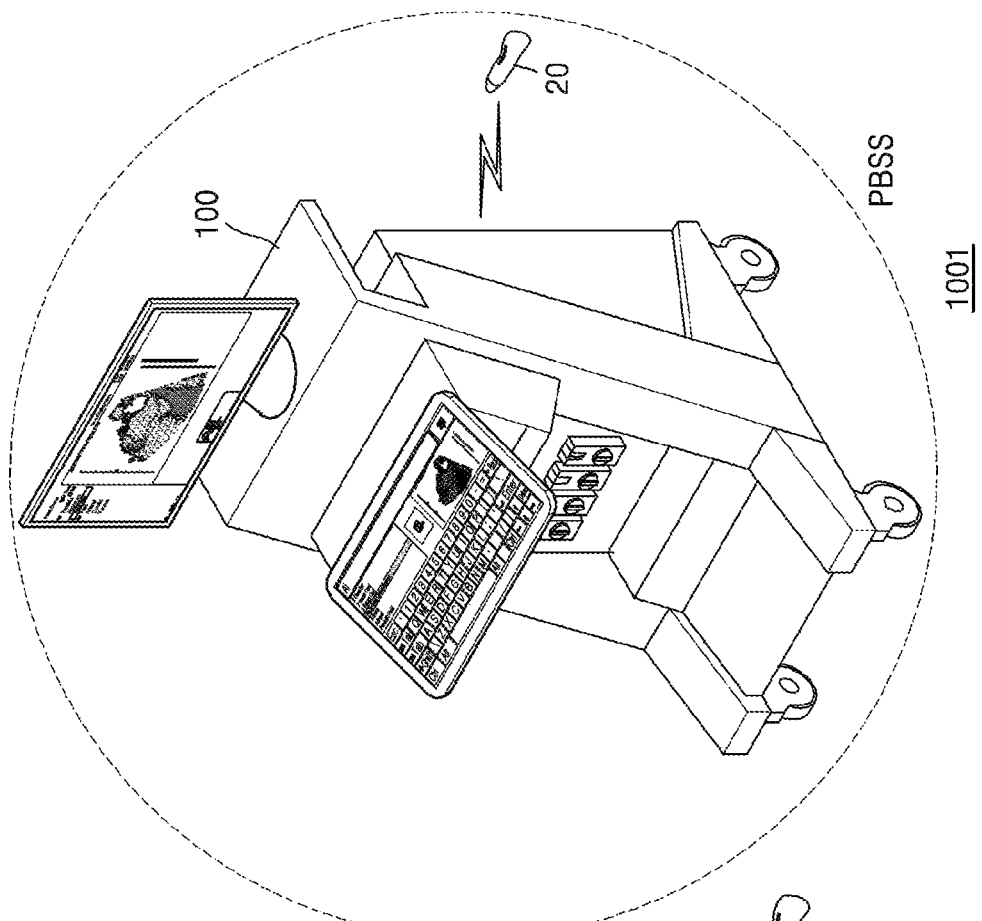
FIGS. 1A and 1B are diagrams showing examples of ultrasound diagnosis systems according to exemplary embodiments.

Reference will now be made in detail to exemplary embodiments, examples of which are illustrated in the accompanying drawings, wherein like reference numerals refer to like structural elements throughout. In this regard, the present exemplary embodiments may have different forms and should not be construed as being limited to the descriptions set forth herein. Accordingly, the exemplary embodiments are merely described below, by referring to the figures, to explain aspects of the present description. Expressions such as "at least one of," when preceding a list of elements, modify the entire list of elements and do not modify the individual elements of the list.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the invention.

Throughout the specification, it will also be understood that when a component "includes" an element, unless there is another opposite description thereto, it should be understood that the component does not exclude another element and may further include another element. In addition, terms such as " ... unit", " ... module", or the like refer to units that perform at least one function or operation, and the units may be implemented as hardware or software or as a combination of hardware and software.

Throughout the specification, an 'ultrasound image' refers to an image of an object or a region of interest (ROI) of the object, which is obtained using ultrasound waves. In this case, an ROI is a region of an object, such as a lesion, which a user desires to observe carefully.

Furthermore, an "object" may be a human, an animal, or a part of a human or animal. For example, the object may be an organ (e.g., the liver, heart, womb, brain, breast, or abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to a human body.

Throughout the specification, a "user" may be, but is not limited to, a medical expert, for example, a medical doctor, a nurse, a medical laboratory technologist, or a medical imaging expert, or a technician who repairs medical apparatuses.

Embodiments of the invention now will be described more fully hereinafter with reference to the accompanying drawings, in which illustrative embodiments of the invention are shown.

Figure 1A:
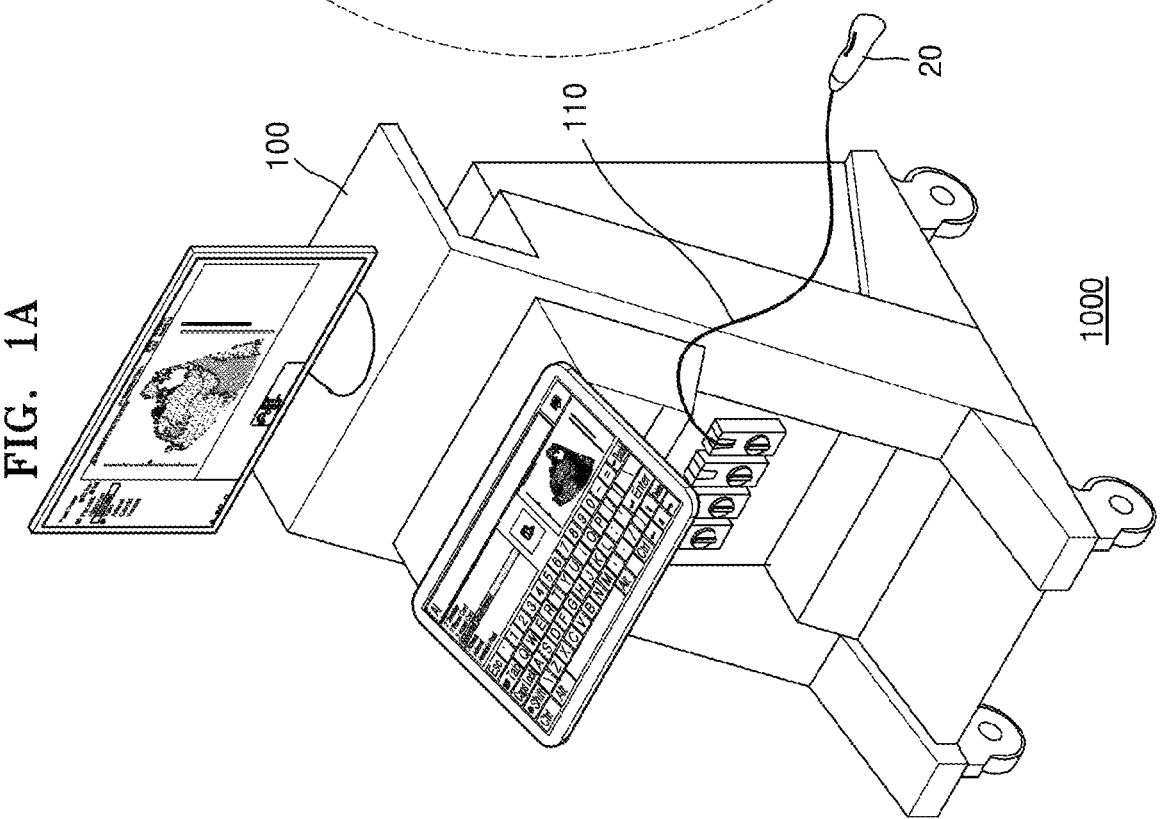

FIGS. 1A and 1B are diagrams showing examples of ultrasound diagnosis systems 1000 and 1001 according to exemplary embodiments.

Referring to FIG. 1A, in the ultrasound diagnosis system 1000, a probe 20 may be connected to an ultrasound imaging device 100 via a wire. In other words, the probe 20 for transmitting and receiving ultrasound signals may be connected to a main body of the ultrasound diagnosis system 1000, i.e., the ultrasound imaging device 100 through a cable 110.

Referring to FIG. 1B, in the ultrasound diagnosis system 1001, a probe 20 may be connected wirelessly to an ultrasound imaging device 100. In other words, the probe 20 may be connected to the ultrasound imaging device 100 via the same wireless network. For example, the probe 20 and the ultrasound imaging device 100 may associate with an mmWave-based wireless network and transmit echo signals received via transducers to the ultrasound imaging device 100 in a 60 GHz frequency band. The ultrasound imaging device 100 may generate ultrasound images of various modes by using echo signals received in the 60 GHz frequency band and display the generated ultrasound images. In this case, the mmWave-based wireless network may use a wireless communication method that is compliant with the WiGig standard developed by the Wireless Gigabit Alliance (WGA), but is not limited thereto.

Figure 2:
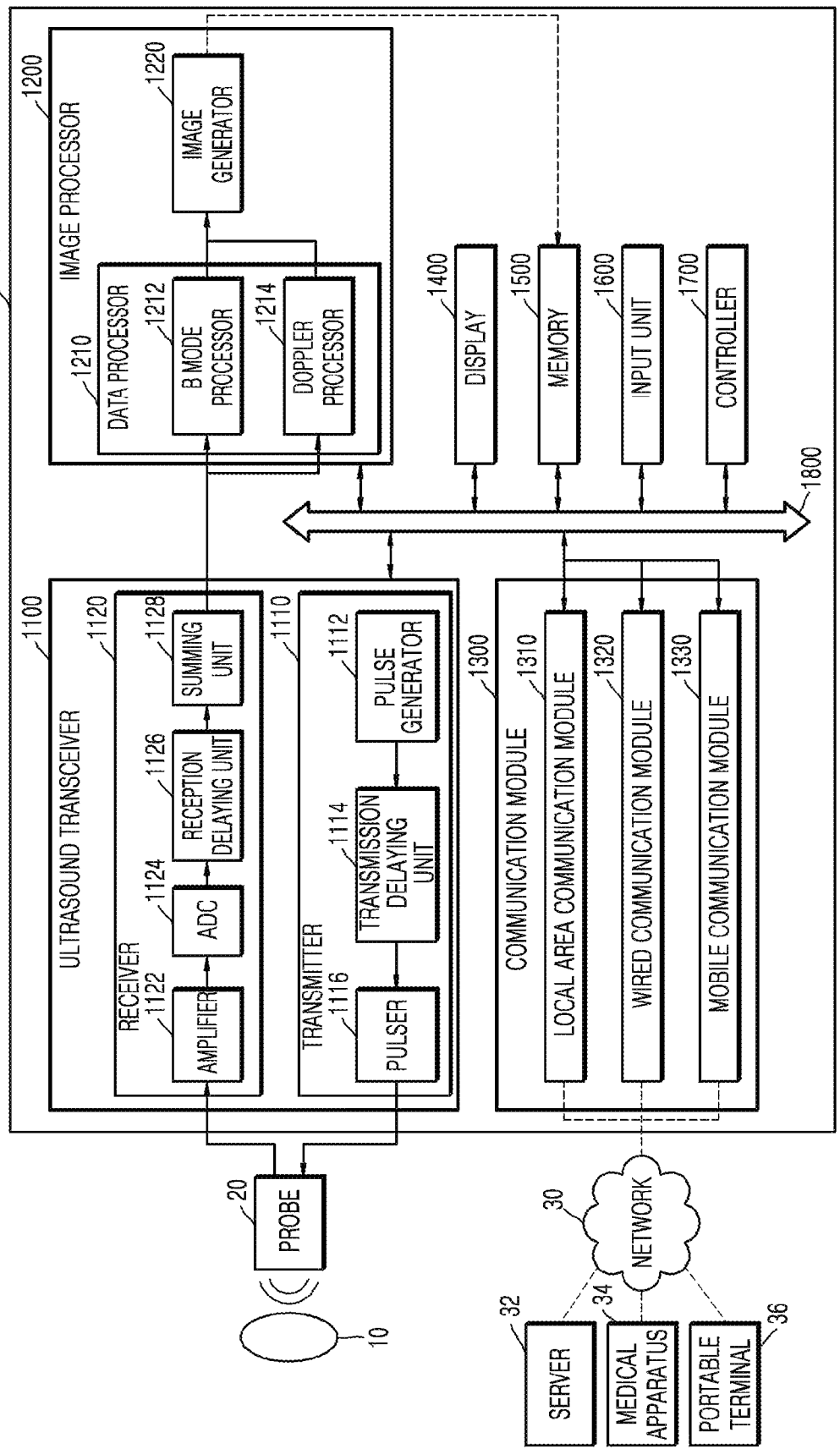
FIG. 2 is a block diagram of a configuration of an ultrasound diagnosis system according to an exemplary embodiment.

FIG. 2 is a block diagram illustrating an ultrasound diagnosis system according to an exemplary embodiment.

Referring to FIG. 2, an ultrasound diagnosis system 1002 may include a probe 20 and an ultrasound imaging device 100. Referring to FIG. 2, the ultrasound imaging device 100 may include an ultrasound transceiver 1100, an image processor 1200, a communication module 1300, a display 1400, a memory 1500, an input unit 1600, and a controller 1700, which may be connected to one another via buses 1800.

In some embodiments, the ultrasound diagnosis system 1002 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 may transmit ultrasound waves to an object 10 (or, a region of interest in the object 10) in response to a driving signal applied by the ultrasound transceiver 1100 and receives echo signals reflected by the object 10 (or, the region of interest in the object 10). The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis system 1002 by wire or wirelessly, and according to embodiments, the ultrasound diagnosis system 1002 may include a plurality of probes 20.

A transmitter 1110 supplies a driving signal to the probe 20. The transmitter 110 includes a pulse generator 1112, a transmission delaying unit 1114, and a pulser 1116. The pulse generator 1112 generates pulses for forming transmission ultrasound waves based on a predetermined pulse repetition frequency (PRF), and the transmission delaying unit 1114 delays the pulses by delay times necessary for determining transmission directionality. The pulses which have been delayed correspond to a plurality of piezoelectric vibrators included in the probe 20, respectively. The pulser 1116 applies a driving signal (or a driving pulse) to the probe 20 based on timing corresponding to each of the pulses which have been delayed.

A receiver 1120 generates ultrasound data by processing echo signals received from the probe 20. The receiver 120 may include an amplifier 1122, an analog-to-digital converter (ADC) 1124, a reception delaying unit 1126, and a summing unit 1128. The amplifier 1122 amplifies echo signals in each channel, and the ADC 1124 performs analog-to-digital conversion with respect to the amplified echo signals. The reception delaying unit 1126 delays digital echo signals output by the ADC 124 by delay times necessary for determining reception directionality, and the summing unit 1128 generates ultrasound data by summing the echo signals processed by the reception delaying unit 1166. In some embodiments, the receiver 1120 may not include the amplifier 1122. In other words, if the sensitivity of the probe 20 or the capability of the ADC 1124 to process bits is enhanced, the amplifier 1122 may be omitted.

The image processor 1200 generates an ultrasound image by scan-converting ultrasound data generated by the ultrasound transceiver 1100. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 1212 extracts B mode components from ultrasound data and processes the B mode components. An image generator 1220 may generate an ultrasound image indicating signal intensities as brightness based on the extracted B mode components 1212.

Similarly, a Doppler processor 1214 may extract Doppler components from ultrasound data, and the image generator 1220 may generate a Doppler image indicating a movement of an object as colors or waveforms based on the extracted Doppler components.

According to an embodiment, the image generator 1220 may generate a three-dimensional (3D) ultrasound image via volume-rendering with respect to volume data and may also generate an elasticity image by imaging deformation of the object 10 due to pressure. Furthermore, the image generator 1220 may display various pieces of additional information in an ultrasound image by using text and graphics. In addition, the generated ultrasound image may be stored in the memory 1500.

The image processor 1200 may segment a shape of an object from an ultrasound image.

A display 1400 displays the generated ultrasound image. The display 1400 may display not only an ultrasound image, but also various pieces of information processed by the ultrasound imaging system 1002 on a screen image via a graphical user interface (GUI). In addition, the ultrasound diagnosis apparatus 1000 ultrasound diagnosis system 1000 may include two or more displays 1400 according to embodiments.

Furthermore, the display 1400 displays a body marker selected according to a user input. The display 1400 also displays a second body marker generated by the controller 1700.

The communication module 1300 is connected to a network 30 by wire or wirelessly to communicate with an external device or a server. Furthermore, if the probe 20 is connected to the ultrasound imaging device 100 via a wireless network, the communication module 1300 may communicate with the probe 20.

The communication module 1300 may exchange data with a hospital server or another medical apparatus in a hospital, which is connected thereto via a PACS. Furthermore, the communication module 1300 may perform data communication according to the digital imaging and communications in medicine (DICOM) standard.

The communication module 1300 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 1300 may receive information about a diagnosis history or medical treatment schedule of a patient from a server and utilizes the received information to diagnose the patient. Furthermore, the communication module 1300 may perform data communication not only with a server or a medical apparatus in a hospital, but also with a portable terminal of a medical doctor or patient.

The communication module 1300 is connected to the network 30 by wire or wirelessly to exchange data with a server 32, a medical apparatus 34, or a portable terminal 36. The communication module 1300 may include one or more components for communication with external devices. For example, the communication module 1300 may include a local area communication module 1310, a wired communication module 1320, and a mobile communication module 1330.

The local area communication module 1310 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 1320 refers to a module for communication using electric signals or optical signals. Examples of wired communication techniques according to an embodiment may include communication via a twisted pair cable, a coaxial cable, an optical fiber cable, and an Ethernet cable.

The mobile communication module 1330 transmits or receives wireless signals to or from at least one selected from a base station, an external terminal, and a server on a mobile communication network. The wireless signals may be voice call signals, video call signals, or various types of data for transmission and reception of text/multimedia messages.

The memory 1500 stores various data processed by the ultrasound diagnosis system 1000. For example, the memory 1500 may store medical data related to diagnosis of an object 10, such as ultrasound data and an ultrasound image that are input or output, and may also store algorithms or programs which are to be executed in the ultrasound imaging system 1002.

The memory 1500 may store a plurality of previously generated body markers and a body marker generated by the controller 1700.

The memory 1500 may be any of various storage media, e.g., a flash memory, a hard disk drive, EEPROM, etc. Furthermore, the ultrasound imaging system 1002 may utilize web storage or a cloud server that performs the storage function of the memory 1500 online.

The input unit 1600 refers to a device via which a user inputs data for controlling the ultrasound diagnosis system 1002. Examples of the input unit 1600 may include hardware components, such as a keypad, a mouse, a touch panel, a touch screen, a track ball, and a jog switch, and software modules for operating the hardware components. However, embodiments are not limited thereto, and the input unit 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

Furthermore, the input unit 1600 may receive a user input for selecting one from among a plurality of body markers prestored in the memory 1500.

The controller 1700 may control all operations of the ultrasound diagnosis apparatus 1000 ultrasound diagnosis system 1000. In other words, the controller 1700 may control operations among the probe 20, the ultrasound transceiver 1100, the image processor 1200, the communication module 1300, the display 1400, the memory 1500, and the input unit 1600 shown in FIG. 1.

According to an exemplary embodiment, the controller 1700 compares a shape of an object depicted in a medical image (e.g., an ultrasound image) with a first body marker. In this case, the first body marker may be one of a plurality of body markers that are preset regardless of a shape or position of the object in the medical image and stored in the memory 1500.

Furthermore, the controller 1700 detects a portion corresponding to the shape of the object from the first body marker according to a comparison result. The controller 1700 also generates a second body marker by emphasizing the detected portion in the first body marker. In this case, each of the first and second body markers may include a body marker having a two-dimensional (2D) shape (hereinafter, referred to as a '2D body marker') or a body marker having a 3D shape (hereinafter, referred to as a '3D body marker').

In one exemplary embodiment, the controller 1700 may detect a portion corresponding to a shape of an object from a first body marker and indicate the detected portion as a line having a different thickness than that of a line depicting the first body marker. For example, if a first body marker is indicated by a 1 mm thick solid line, the controller 1700 may generate a second body marker having a portion in the first body marker corresponding to a shape of an object indicated by a 2 mm or 0.5 mm thick solid line. As another example, the controller 1700 may generate a second body marker in which a portion of the first body marker corresponding to the shape of the object is indicated by a 1 mm thick broken line. The thicknesses of the lines are merely examples provided for convenience of explanation, and exemplary embodiments are not limited thereto.

According to another exemplary embodiment, the controller 1700 may detect a portion corresponding to a shape of an object from a first body marker and indicate the detected portion as a color different from a color representing the first body marker. For example, if a first body marker is indicated by a white line, the controller 1700 may generate a second body marker having a portion of the first body marker corresponding to a shape of an object indicated by a red line. The colors of the lines are merely examples provided for convenience of explanation, and exemplary embodiments are not limited thereto.

According to another exemplary embodiment, the controller 1700 may detect a portion corresponding to a shape of an object from a first body marker and indicate the detected portion as being larger than the remaining portions of the first body marker. In other words, the controller 1700 may generate a second body marker in which only a portion of the first body marker corresponding to a shape of the object has been enlarged.

Furthermore, the controller 1700 may partition a first body marker into a plurality of portions.

According to an exemplary embodiment, the controller 1700 may partition a first body marker into a plurality of portions that include a portion corresponding to a shape of an object in a medical image. In another exemplary embodiment, the controller 1700 may partition the first body marker into a plurality of portions according to prestored anatomical theory. The controller 1700 may also indicate the portion including the shape of the object among the plurality of portions as a line or color that is different from a line or color representing the first body marker. Furthermore, the controller 1700 may enlarge the portion including the shape of the object among the plurality of portions, compared to the remaining portions of the first body marker.

All or some of the probe 20, the ultrasound transceiver 1100, the image processor 1200, the communication module 1300, the display 1400, the memory 1500, the input unit 1600, and the controller 1700 may be implemented as software modules. Furthermore, at least one selected from the ultrasound transceiver 1100, the image processor 1200, and the communication module 1300 may be included in the controller 1700. However, embodiments of the present invention are not limited thereto.

Figure 3:
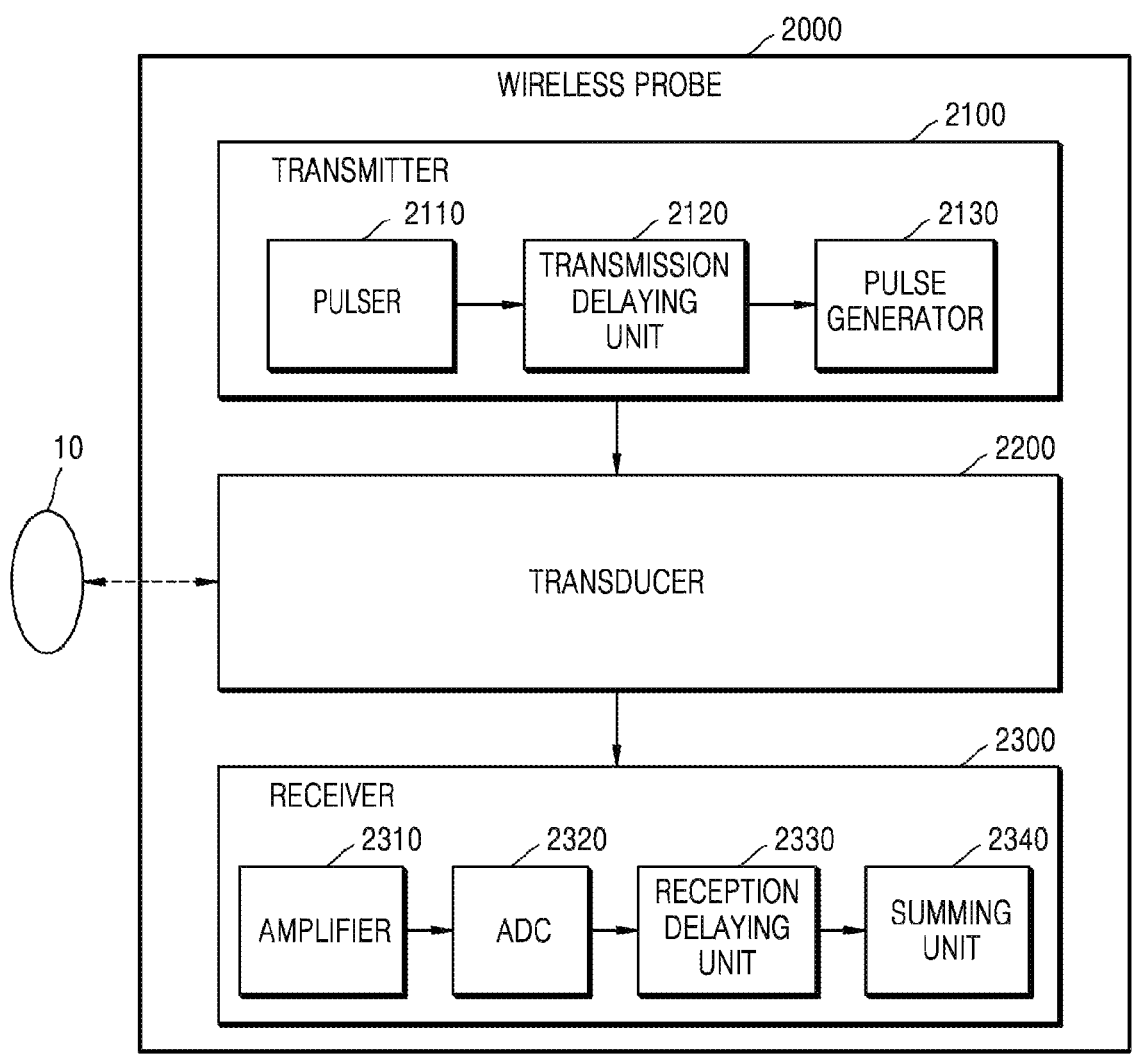
FIG. 3 is a block diagram of a configuration of a wireless probe according to an exemplary embodiment.

FIG. 3 is a block diagram of a configuration of a wireless probe 2000 according to an exemplary embodiment.

Referring to FIG. 3, as described above with reference to FIG. 2, the wireless probe 2000 according to the present exemplary embodiment may include a plurality of transducers 2200, and, according to exemplary embodiments, may include some or all of the components of the ultrasound transceiver 1100 shown in FIG. 2.

The wireless probe 2000 according to the embodiment shown in FIG. 3 includes a transmitter 2100, a transducer 2200, and a receiver 2300. Since descriptions thereof are given above with reference to FIG. 2, detailed descriptions thereof will be omitted here. In addition, according to embodiments, the wireless probe 2000 may selectively include a reception delaying unit 2330 and a summing unit 2340.

The wireless probe 2000 may transmit ultrasound signals to the object 10, receive echo signals from the object 10, generate ultrasound data, and wirelessly transmit the ultrasound data to the ultrasound imaging system 1002 shown in FIG. 2.

Figure 4:
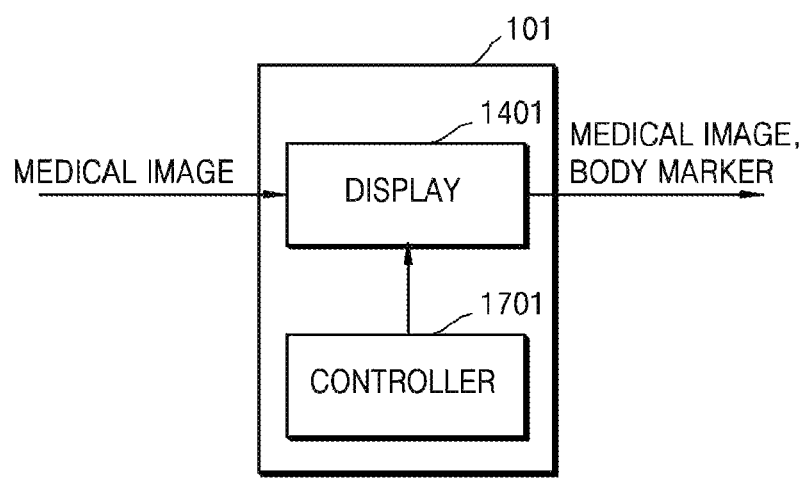
FIG. 4 is a block diagram of an apparatus for generating a body marker according to an exemplary embodiment.

FIG. 4 is a block diagram of an apparatus 101 for generating a body marker (hereinafter, referred to as a 'body marker generating apparatus') according to an exemplary embodiment.

Referring to FIG. 4, the body marker generating apparatus 101 includes a controller 1701 and a display 1401. All or some of the controller 1701 and the display 1401 may be implemented as software modules. However, exemplary embodiments are not limited thereto, and some of the above components may be implemented as hardware modules. Furthermore, the display 1401 may include an independent control module.

Furthermore, the controller 1701 and the display 1401 may correspond to as the controller 1700 and the display 1401 shown in FIG. 2, respectively. If the body marker generating apparatus 101 is included in the ultrasound imaging device 100, the body marker generating apparatus 101 may further include the ultrasound transceiver 1100, the image processor 1200, the communication module 1300, the memory 1500, and the input unit 1600 shown in FIG. 2, as well as the controller 1701 and the display 1401.

The controller 1701 compares a first body marker with a shape of the object (10 of FIG. 2) and then detects a portion corresponding to the shape of the object 10 from the first body marker. In this case, the first body marker is one of a plurality of body markers stored in a memory (not shown) of the body marker generating apparatus 101.

A body marker refers to a picture that is attached to a medical image such as an ultrasound image to allow a viewer (e.g., a user) to easily identify the object 10 shown in the medical image when observing the medical image.

According to an exemplary embodiment, a first body marker means a body marker produced in advance and stored in the body marker generating apparatus 101. In other words, the first body marker is generated in advance by a manufacturer or user without taking into account information about a current position of the object 10 shown in a medical image Since a first body marker does not reflect a current position of the object 10, even if the first body marker is attached to a medical image, it may be difficult for a viewer to determine an accurate position of the object 10 when observing the medical image. A first body marker will now be described in more detail with reference to FIGS. 5 and 6.

Figure 5:
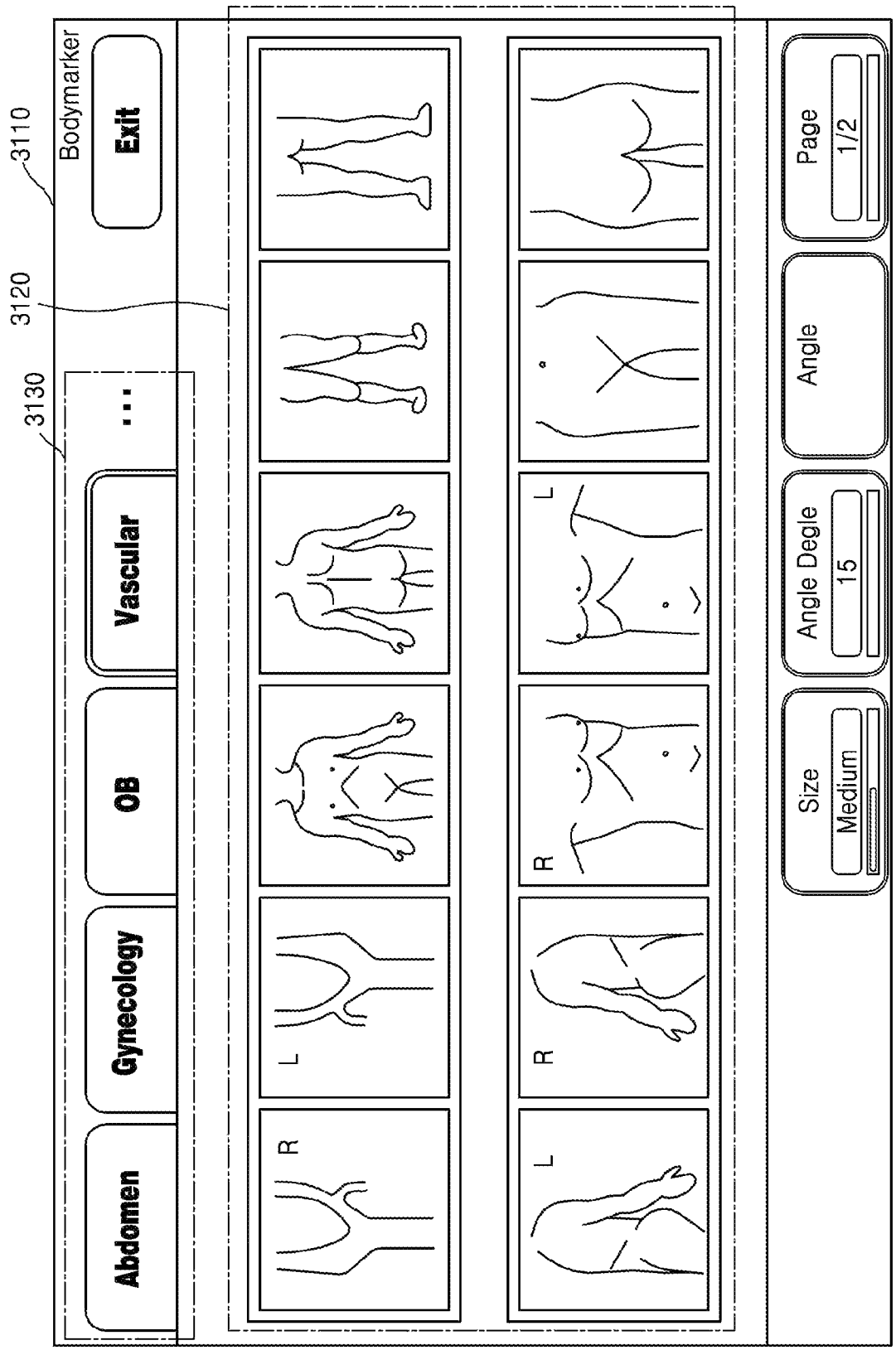
FIGS. 5 and 6 are diagrams for explaining an example of a first body marker according to an exemplary embodiment.
Figure 6:
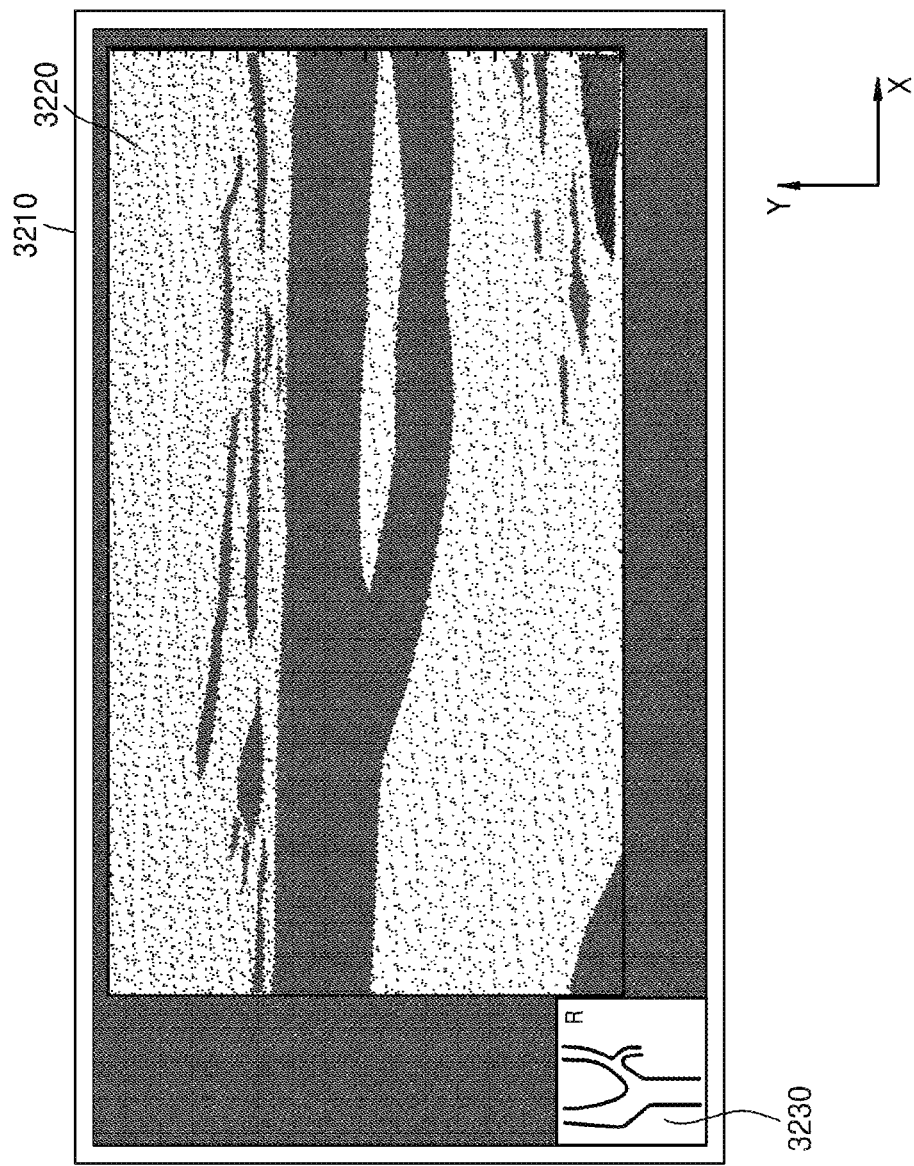

FIGS. 5 and 6 are diagrams for explaining an example of a first body marker according to an exemplary embodiment.

FIG. 5 illustrates an example of a plurality of prestored body markers 3120 output to a screen 3110. Referring to FIGS. 4 and 5, the controller 1701 selects one from among the body markers 3120 as a first body marker, based on the object (10 of FIG. 2) shown in a medical image.

For example, the controller 1701 may select a first body marker based on a user input received via an input unit (not shown). As another example, the controller 1701 may select a first body marker based on a shape of the object 10 segmented from the medical image. Examples where the controller 1701 selects one of the body markers 3120 as the first body marker will be described in more detail below with reference to FIGS. 8 through 13.

The body markers 3120 may be aligned according to the type of application groups 3130. In this case, an application refers to a diagnostic field, and the type of application may be determined based on a part or internal organ of a human or animal body.

For example, the application groups 3130 may include an abdomen group, a small part group including breasts, an oral cavity, a genital organ, etc., a vascular group, a musculoskeletal group, an Obstetrics (OB)/Gynecology (GYN) group, a cardiac group, a brain group, a urology group, and a vet group. However, exemplary embodiments are not limited thereto, and parts or internal organs of a human or animal body may be classified into a plurality of application groups according to a predetermined criterion.

The display 1401 may output the body markers 3120 that are aligned according to the type of application groups 3130 to the screen 3110. For example, if a user selects (e.g., clicks or taps) an icon 'vascular' from among icons representing the application groups 3130 displayed on the screen 3110, the display 1401 may output to the screen 3110 body markers that are included in the vascular group among the body markers 3120.

In this case, since the body markers 3120 are produced in advance for storage, the user has to analyze all the body markers 3120 and then select a first body marker that is the most suitable for the object 10 in a medical image from among the body markers 3120. Thus, it may take a large amount of time for the user to select the first body marker.

Furthermore, the first body marker selected from among the body markers 3120 may not include accurate information about the object 10, as descried in detail with reference to FIG. 6.

FIG. 6 illustrates an example of a medical image 3220 and a first body marker 3230 attached thereto that are output to a screen 3210. For convenience of explanation, it is assumed herein that the medical image 3220 is an ultrasound image representing a portion of a blood vessel.

To help a viewer who sees the medical image 3220 later understand it, the first body marker 3230 may be attached to the medical image 3220. In this case, based on the first body marker 3230, the viewer may only recognize that the medical image 3220 shows a blood vessel but cannot identify which portion of a blood vessel in the first body marker 3230 is shown in the medical image 3220.

For example, a blood vessel shown in the medical image 3220 may correspond to a portion of a blood vessel depicted in the first body marker 3230. Otherwise, the blood vessel shown in the medical image 3220 may correspond to a wider area including the blood vessel depicted in the first body marker 3230. However, since the first body marker 3230 is produced in advance and cannot be modified, the first body marker 3230 cannot accurately indicate which portion of the blood vessel depicted in the first body marker 3230 corresponds to the blood vessel in the medical image 3220.

As described above with reference to FIGS. 5 and 6, a first body marker that is generated in advance may not accurately represent current information about the object 10 shown in a medical image.

In addition, according to an exemplary embodiment, the controller 1701 may generate a second body marker by emphasizing a portion in the first body marker 3230 corresponding to an object (i.e., a blood vessel) shown in the medical image 3220. Thus, the second body marker may accurately represent current information about the object in the medical image 3220. The second body marker will now be described in more detail with reference to FIG. 7.

Figure 7A:
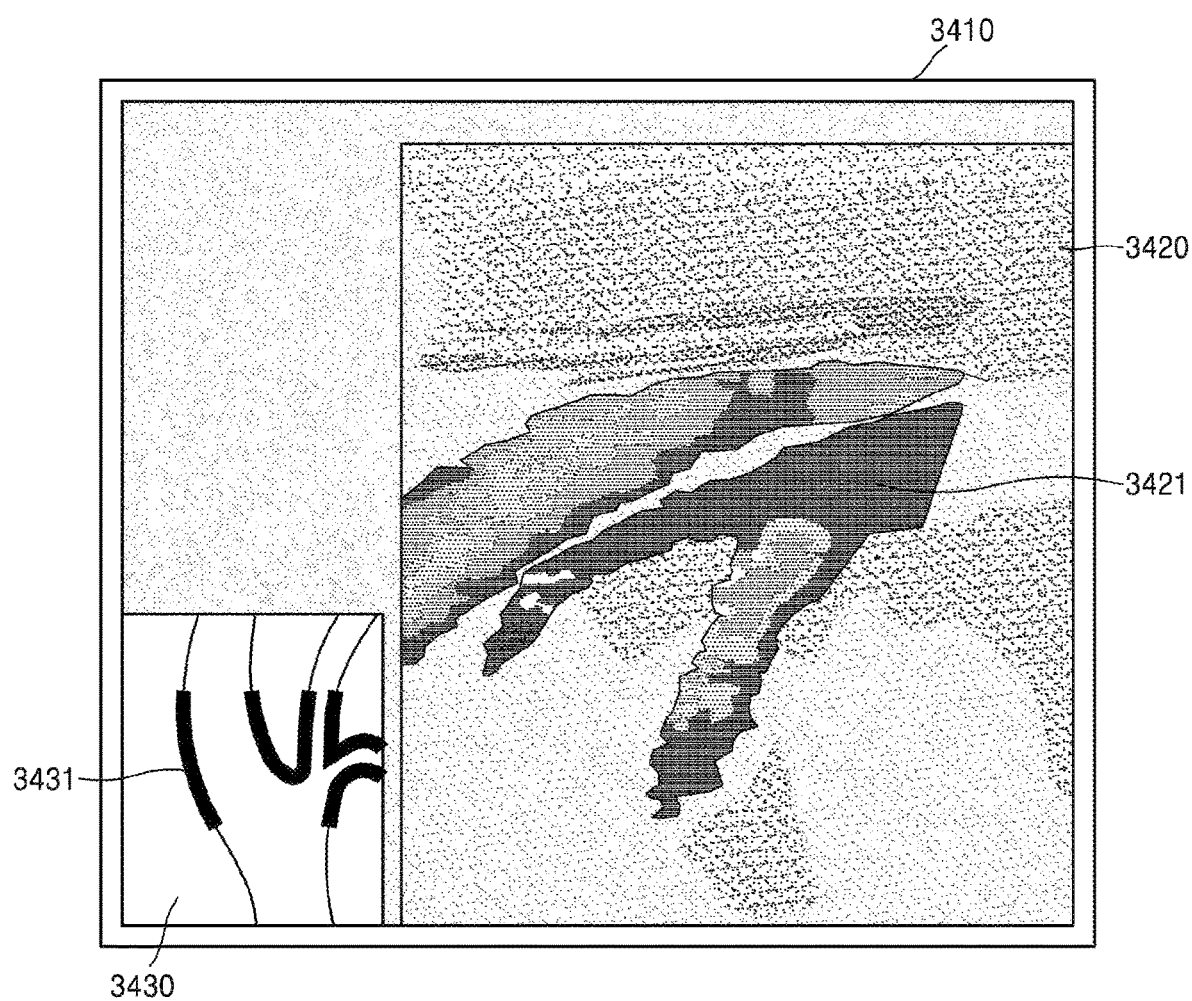
FIG. 7A is a diagram for explaining an example of a second body marker according to an exemplary embodiment.

FIG. 7A is a diagram for explaining an example of a second body marker according to an exemplary embodiment.

FIG. 7A illustrates an example of a medical image 3420 and a second body marker 3430 attached thereto that are output to a screen 3410. For convenience of explanation, it is assumed herein that the medical image 3420 is an ultrasound image of a blood vessel 3421. In the medical image 3420, some blood vessels distributed in vivo are enlarged.

As described above with reference to FIG. 6, a first body marker attached to the medical image 3420 includes only information about the type of the blood vessel 3421 shown in the medical image 3420. For example, the first body marker may represent whether the blood vessel 3421 is a coronary artery or pulmonary artery. Thus, the first body marker cannot provide a person who views the medical image 3420 with accurate information indicating which portion of a coronary artery corresponds to the blood vessel 3421.

A portion 3431 corresponding to the blood vessel 3421 is indicated in the second body marker 3430 to distinguish from the remaining portions. In other words, the controller 1701 may generate the second body marker 3430 in which the portion 3431 of the first body marker corresponding to the blood vessel 3421 has been emphasized. For example, the controller 1701 may indicate the portion 3431 of the first body marker corresponding to the blood vessel 3421 as a line having a different thickness than that of a line indicating the remaining portions. As another example, the controller 1701 may indicate the portion 3431 of the first body marker corresponding to the blood vessel 3421 as a color other than a color representing the remaining portions. Thus, a viewer who sees the medical image 3420 may accurately identify a position of the blood vessel 3421 included in the medical image 3420.

In addition, the first body marker or the second body marker 3430 may comprise a 3D body marker, as described in detail with reference to FIG. 7B.

Figure 7B:
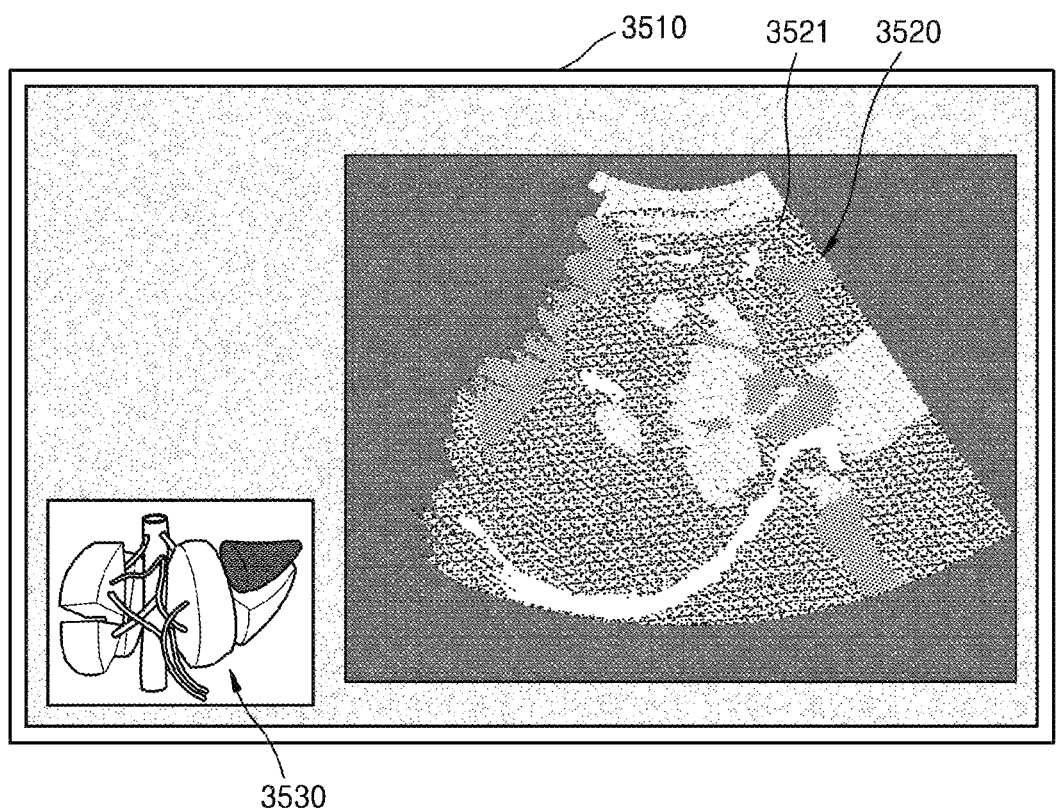
FIG. 7B shows an example of a three-dimensional (3D) body marker according to an exemplary embodiment.

FIG. 7B is a diagram for explaining an example of a 3D body marker according to an exemplary embodiment.

FIG. 7B illustrates an example of a medical image 3520 and a second body marker 3530 added thereto that are output on a screen 3510. In this case, the second body marker 3530 may include a 3D body marker. For convenience of explanation, it is assumed herein that the medical image 3520 is an ultrasound image showing a region 3521 of the liver.

In general, a first body marker added to the medical image 3520 includes only information about the type of an organ depicted in the medical image 3520. For example, since the first body marker represents the entire shape of the liver, a viewer who sees the medical image 3520 may not be able to determine which portion of the liver is shown in the medical image 3520 based on the first body marker only.

In addition, the region 3521 of the liver is indicated in the second body marker 3530 to distinguish it from the other regions of the liver in the medical image 3520. In other words, the controller 1701 generates the second body marker 3530 in which the region 3521 in the medical image 3520 has been emphasized as compared with the first body marker. For example, the controller 1701 may partition the liver depicted in the first body marker into a plurality of portions. The controller 1701 may then generate the second body marker 3530 by emphasizing a portion that includes the region 3521 shown in the medical image 3520 among the plurality portions. For example, a portion including the region 3521 shown in the medical image 3520 may be indicated in the second body marker 3530 as a line having a different thickness than that of the remaining portions. As another example, a portion including the region 3521 shown in the medical image 3520 may be indicated in the second body marker 3530 by a color that is different from that of the remaining portions. Thus, a viewer who sees the medical image 3520 is able to accurately identify which portion of the liver corresponds to the region 3521 of the liver in the medical image 3520.

While FIG. 7B shows that the second body marker 3530 includes a 3D body marker, the first body marker may also include a 3D body marker.

Referring back to FIG. 4, the display 1401 outputs a medical image showing the object 10 to a screen. The display 1401 may also outputs a second body marker generated by the controller 1701 to the screen. In this case, the display 1401 may output first and second body markers together to a single screen.

Examples of selection of a first body marker from among a plurality of prestored body markers will now be described with reference to FIGS. 8 through 13B.

Figure 8:
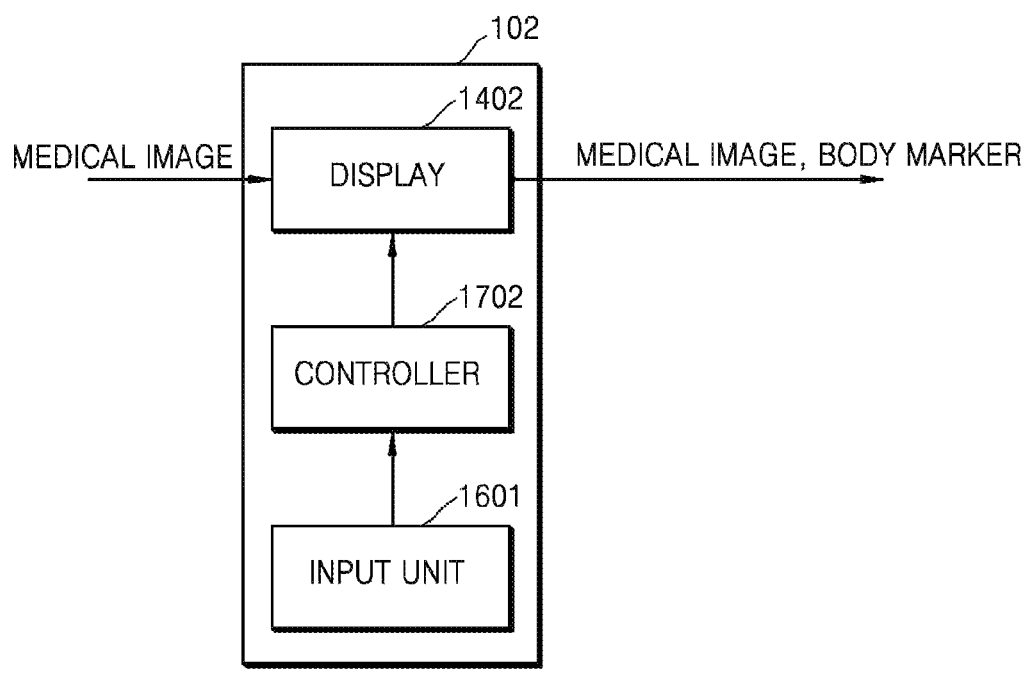
FIG. 8 is a block diagram of an apparatus for generating a body marker according to another exemplary embodiment.

FIG. 8 is a block diagram of a body marker generating apparatus 102 according to another exemplary embodiment.

Referring to FIG. 8, the body marker generating apparatus 102 according to the present exemplary embodiment includes a controller 1702, a display 1402, and an input unit 1601. In this case, all or some of the controller 1702, the display 1402, and the input unit 1601 may be implemented as software modules. However, exemplary embodiments are not limited thereto, and some of the above components may be implemented as hardware modules. Furthermore, the display 1401 and the input unit 1601 may each include an independent control module.

Furthermore, the controller 1702 and the display 1402 may have the same configurations as the controller 1702 and the display 1401 shown in FIG. 4, respectively. The input unit 1601 may also have the same configuration as the input unit 1600 shown in FIG. 2. If the body marker generating apparatus 102 is included in the ultrasound imaging apparatus (100 of FIG. 2), the body marker generating apparatus 102 may further include the ultrasound transceiver 1100, the image processor 1200, the communication module 1300, and the memory 1500 shown in FIG. 2, as well as the controller 1702, the display 1402, and the input unit 1601.

Since the display 1402 performs the same operations as described above with reference to FIGS. 1 through 7, a detailed description of the display 1402 is omitted.

The input unit 1601 receives a user input for designating one from among a plurality of prestored body markers. For example, a user may select a body marker similar to the object 10 after viewing a medical image output to the display 1402.

The controller 1702 selects a first body marker based on a user input received from the input unit 1601. The controller 1702 also generates a second body marker in which a portion of the first body marker corresponding to the object 10 has been emphasized. An example where the input unit 1601 receives a user input and then the controller 1702 selects a first body marker will now be described in detail with reference to FIGS. 9A and 9B.

Figure 9A:
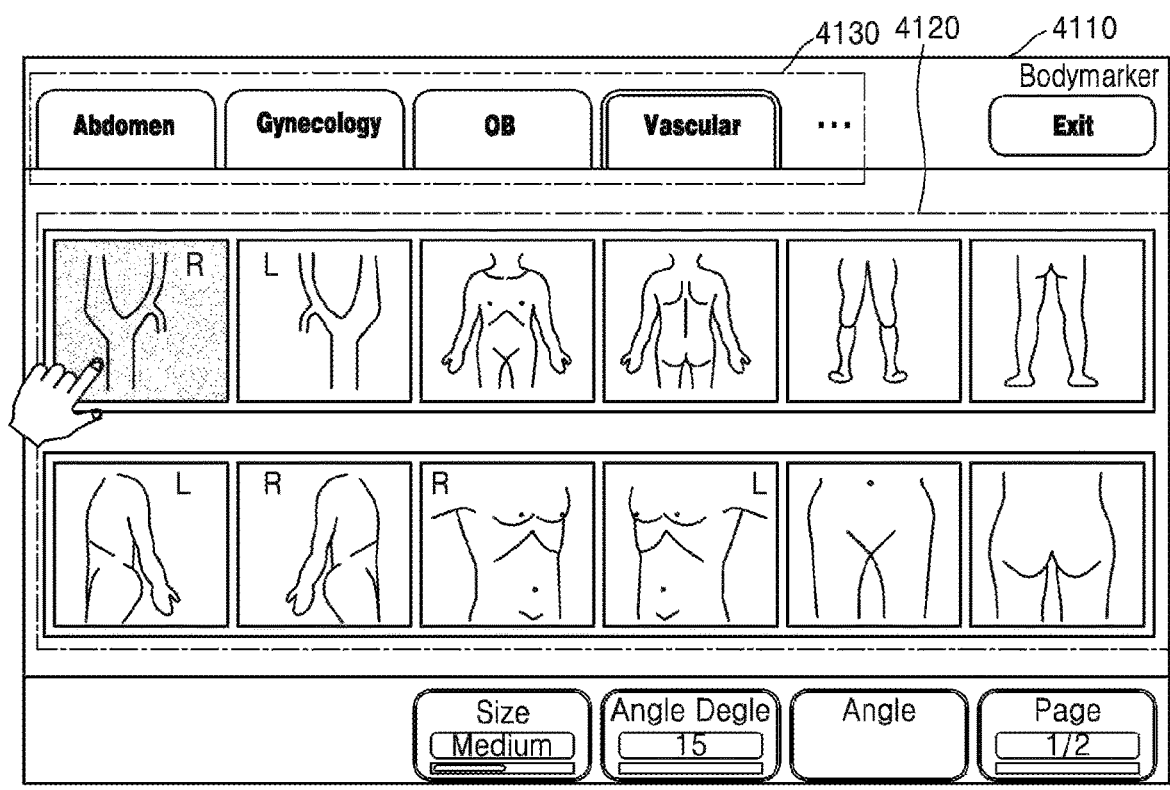
FIGS. 9A and 9B are diagrams for explaining an example where an input unit receives a user input for designating a first body marker according to an exemplary embodiment.
Figure 9B:
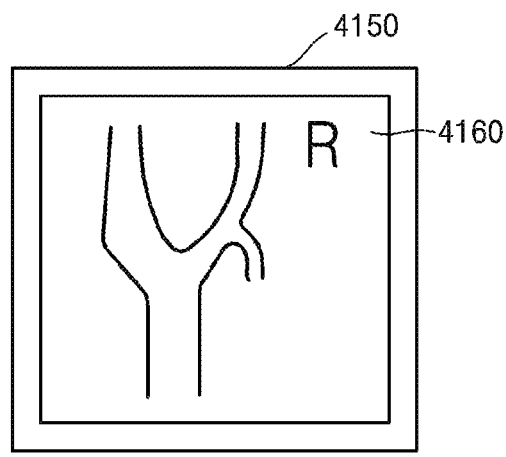

FIGS. 9A and 9B are diagrams for explaining an example where the input unit 1601 receives a user input for designating a first body marker according to an exemplary embodiment.

Referring to FIG. 9A, a plurality of body markers 4120 prestored in the body marker generating apparatus 102 are output to a screen 4110. In this case, the body markers 4120 may be aligned according to the type of application groups 4130, as described above with reference to FIG. 4.

A user may designate one 4140 from among the body markers 4120 output to the screen 4110. For example, if the input unit 1601 includes hardware components, such as a keypad, a mouse, a touch panel, a touch screen, a track ball, a jog switch, etc., and software modules for operating the hardware components, the user may click the one 4140 of the body markers 4120. As another example, if the input unit 1601 includes a touch screen and a software module for operating the same, the user may tap the one 4140 of the body markers 4120.

The controller 1702 selects a first body marker based on a user input. In other words, the controller 1702 may select the body marker 4140 designated by the user as a first body marker. Then, as shown in FIG. 9B, a first body marker 4160 is output to a screen 4150.

Figure 9C:
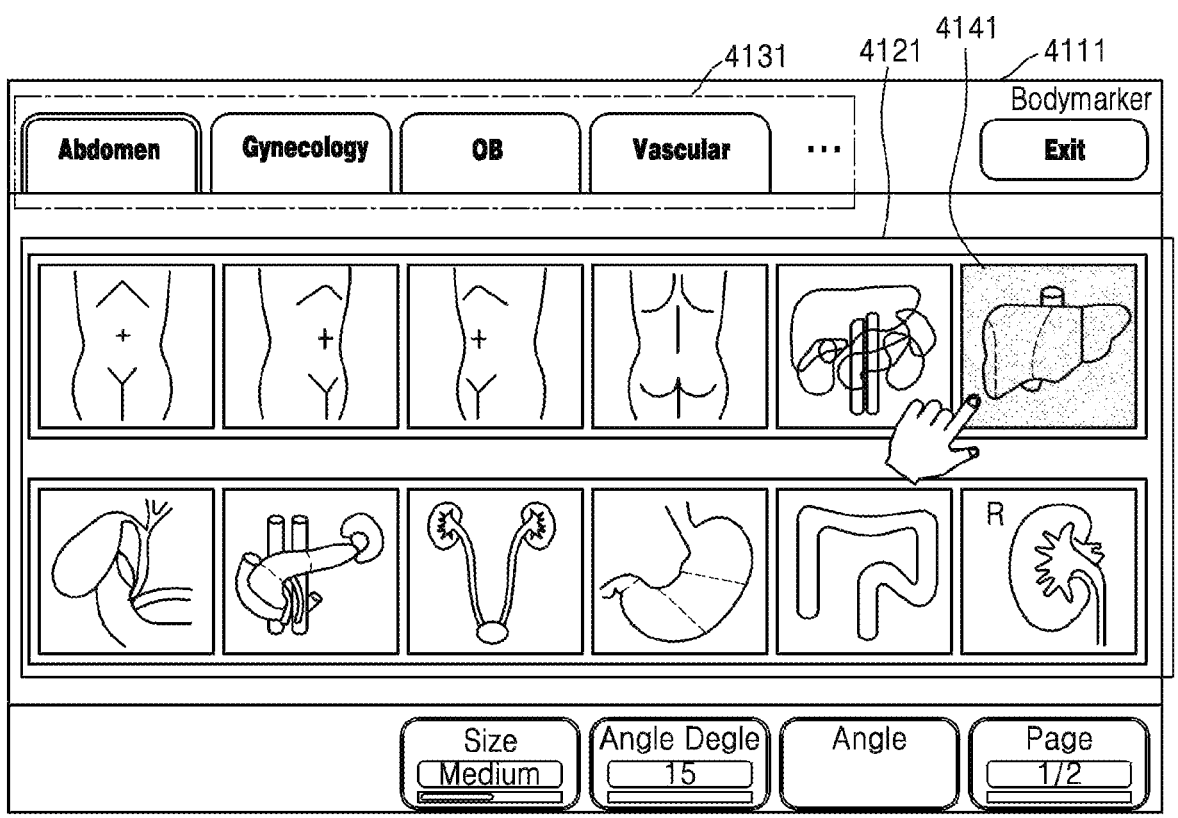
FIGS. 9C and 9D show an example where an input unit receives a user input for designating a first body marker according to another exemplary embodiment.
Figure 9D:
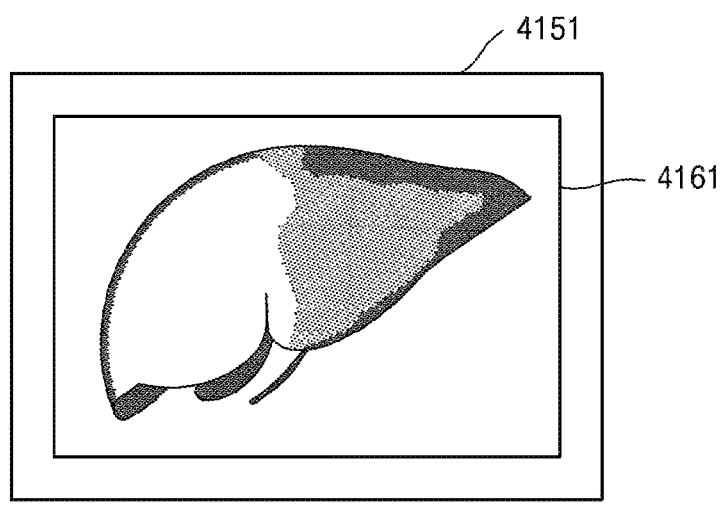

FIGS. 9C and 9D are diagrams for explaining an example where the input unit 1601 receives a user input for designating a first body marker according to another exemplary embodiment.

Referring to FIG. 9C, a plurality of body markers 4121 prestored in the body marker generating apparatus 102 are output on a screen 4111. In this case, the body markers 4121 may be aligned according to the type of application groups 4131, as described above with reference to FIG. 5.

A user may designate one body marker 4141 from among the body markers 4121 output on the screen 4111. An example where the input unit 1601 receives a user input for designating the body marker 4141 is as described above with reference to FIG. 9A.

The body markers 4121 output on the screen 4111 may include 3D body markers. In other words, each of the body markers 4121 may have a 3D shape.

The controller 1702 selects a first body marker based on a user input. In other words, the controller 1702 selects the body marker 4141 designated by the user as the first body marker. For example, if the body markers 4121 output on the screen 4111 are 2D body markers, the controller 1702 may convert the designated body marker 4141 into a 3D body marker and transmit the 3D body marker to the display 1402. As another example, if the body markers 4121 output on the screen 4111 are 3D body markers, the controller 1702 may transmit information about the designated body marker 4141 to the display 1402.

Then, as shown in FIG. 9D, the display 1402 outputs a first body marker 4161 on a screen 4151. In this case, the first body marker 4161 may include a 3D body marker.

As described above with reference to FIGS. 9A through 9D, the controller 1702 determines a body marker designated by the user as a first body marker, but exemplary embodiments are not limited thereto. For example, the controller 1702 may select a first body marker based on a shape of the object 10 shown in a medical image. An example where the controller 1702 selects a first body marker based on a shape of the object 10 will be described in more detail below with reference to FIGS. 10 through 11D.

Figure 10:
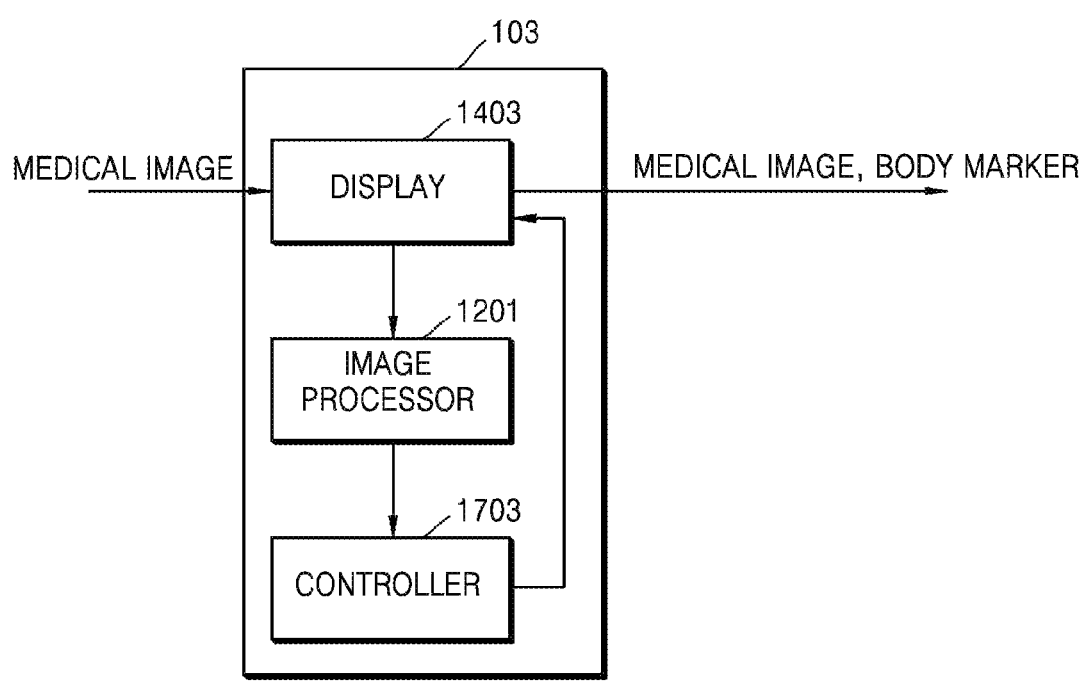
FIG. 10 is a block diagram of a configuration of an apparatus for generating a body marker according to another exemplary embodiment.

FIG. 10 is a block diagram of a configuration of a body marker generating apparatus 103 according to another exemplary embodiment.

Referring to FIG. 10, the body marker generating apparatus 103 according to the present exemplary embodiment includes a controller 1703, a display 1403, and an image processor 1201. In this case, all or some of the controller 1703, the display 1403, and the image processor 1201 may be implemented as software modules. However, exemplary embodiments are not limited thereto, and some of the above components may be implemented as hardware modules. Furthermore, the display 1403 and the image processor 1201 may each include an independent control module.

Furthermore, the controller 1703 and the display 1403 may have the same configurations as the controller 1701 and the display 1401 shown in FIG. 4, respectively. The image processor 1201 may also have the same configuration as the image processor 1200 shown in FIG. 2. If the body marker generating apparatus 103 is included in the ultrasound imaging apparatus (100 of FIG. 2), the body marker generating apparatus 103 may further include the ultrasound transceiver 1100, the communication module 1300, the memory 1500, and the input unit 1600 shown in FIG. 2, as well as the controller 1703, the display 1403, and the image processor 1201.

Since the display 1403 performs the same operations as described above with reference to FIGS. 1 through 9B, a detailed description of the display 1403 is omitted.

The Image generator 1201 segments a shape of the object 10 from a medical image. For example, to do so, the image processor 1201 may detect contours of the object 10 from the medical image and connect the detected contours. In this case, the image processor 1201 may segment the shape of the object 10 by using various methods such as a thresholding method, a K-means algorithm, a compression-based method, a histogram-based method, edge detection, a region-growing method, a partial differential equation-based method, a graph partitioning method, and the like. The above-described methods are obvious to one having general knowledge in the art, detailed descriptions thereof are omitted.

The controller 1703 selects a first body marker based on a shape of the object segmented by the image processor 1201. For example, the controller 1703 may determine a body marker that is the most similar to the shape of the object 10 as the first body marker, from among a plurality of body markers stored in the body marker generating apparatus 103.

The controller 1703 also generates a second body marker in which a portion of the first body marker corresponding to the object 10 has been emphasized. An example where the image processor 1201 segments a shape of the object 10 from a medical image and the controller 1703 selects a first body marker according to an exemplary embodiment will now be described in more detail with reference to FIGS. 11A and 11B.

Figure 11A:
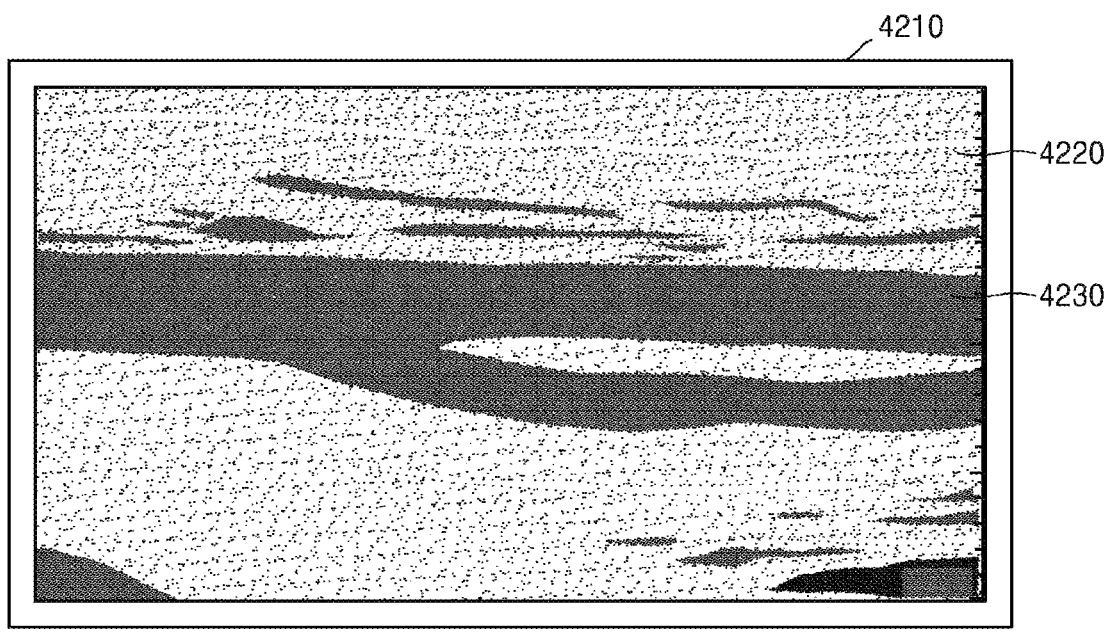
FIGS. 11A and 11B show an example where an image processor segments a shape of an object from a medical image according to an exemplary embodiment.
Figure 11B:
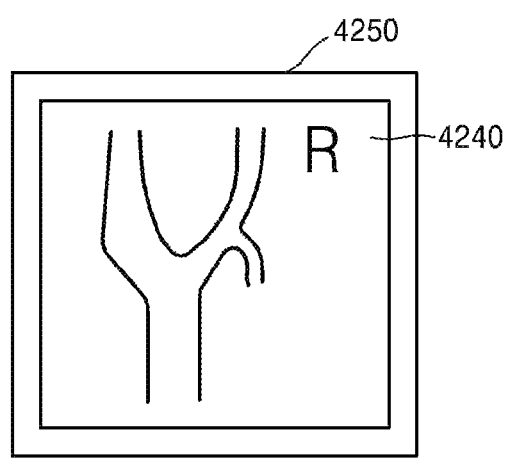

FIGS. 11A and 11B are diagrams for explaining an example where the image processor 1201 segments a shape of an object from a medical image according to an exemplary embodiment.

Referring to FIG. 11A, a medical image 4220 showing an object 4230 is output to a screen 4210. The image processor 1201 segments a shape of the object 4230 in the medical image 4220. For example, the image processor 1201 may segment the shape of the object 4230 in the medical image 4220 by using any one of the segmentation methods described with reference to FIG. 10.

The controller 1703 selects a first body marker based on the shape of the object 4230. For example, the controller 1703 may determine a body marker that is the most similar to the shape of the object 4230 as the first body marker, from among a plurality of body markers stored in the body marker generating apparatus 103. Then, as shown in FIG. 11B, the display 1403 may output a first body marker 4240 to a screen 4250.

Figure 11C:
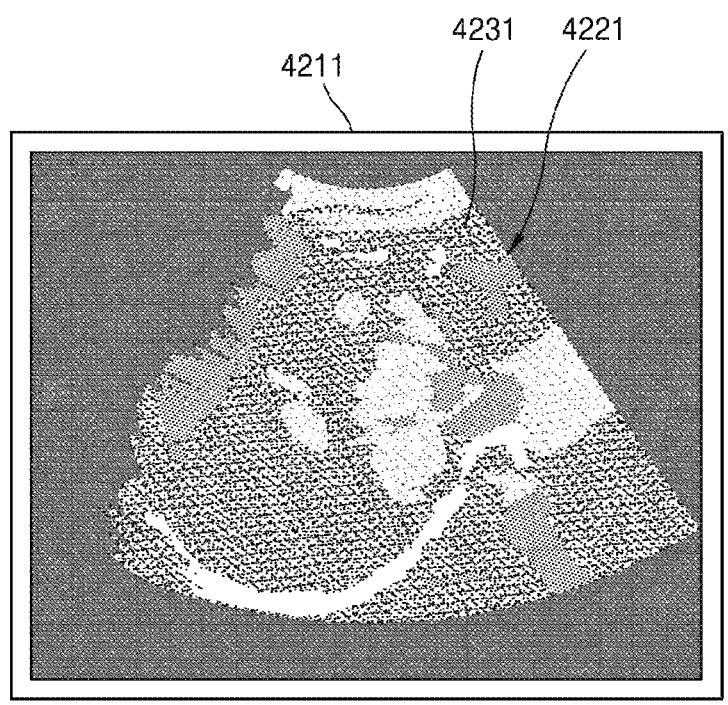
FIGS. 11C and 11D show an example where an image processor segments a shape of an object from a medical image according to another exemplary embodiment.
Figure 11D:
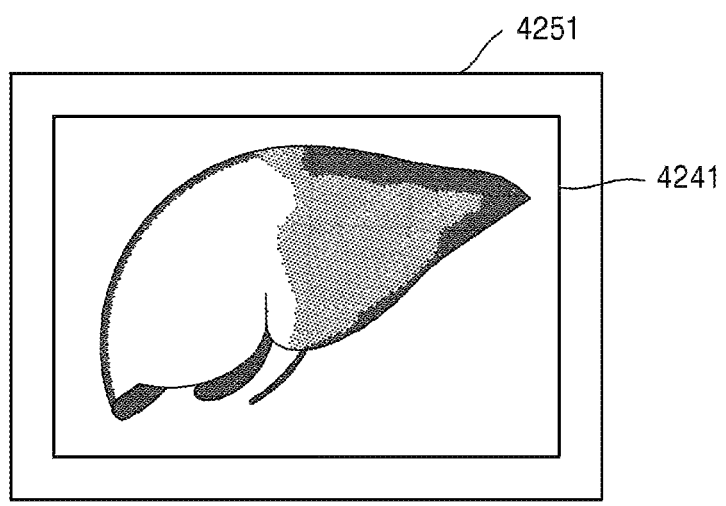

FIGS. 11C and 11D are diagrams for explaining an example where the image processor 1201 segments a shape of an object from a medical image according to another exemplary embodiment Referring to FIG. 11C, a medical image 4221 showing an object 4231 is output to a screen 4211. The image processor 1201 segments a shape of the object 4231 in the medical image 4221. For example, the image processor 1201 may segment the shape of the object 4231 in the medical image 4221 by using any one of the segmentation methods described with reference to FIG. 10.

The controller 1703 selects a first body marker based on the shape of the object 4231. Then, as shown in FIG. 11D, the display 1403 may output a first body marker 4241 to a screen 4251. In this case, the first body marker 4241 may include a body marker having a 3D shape.

In addition, the controller 1703 may change a previously selected first body marker to another body marker according to a user input. An example where the controller 1703 replaces a previously selected first body marker with another body marker will be described in more detail below with reference to FIGS. 12 and 13A through 13D.

Figure 12:
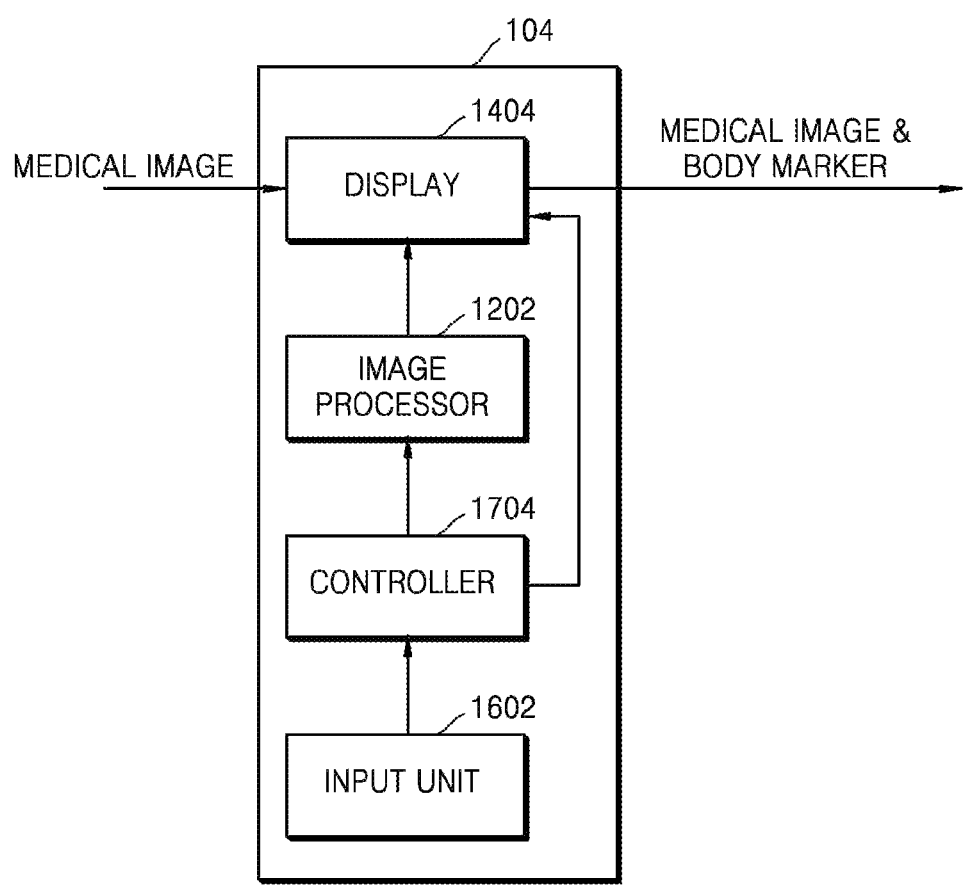
FIG. 12 is a block diagram of an apparatus for generating a body marker according to another exemplary embodiment.

FIG. 12 is a block diagram of a configuration of a body marker generating apparatus 104 according to another exemplary embodiment.

Referring to FIG. 12, the body marker generating apparatus 104 according to the present exemplary embodiment includes a controller 1704, a display 1404, an input unit 1602, and an image processor 1202. In this case, all or some of the controller 1704, the display 1404, the input unit 1602, and the image processor 1202 may be implemented as software modules. However, exemplary embodiments are not limited thereto, and some of the above components may be implemented as hardware modules. Furthermore, the display 1404, the image processor 1202, and the input unit 1602 may each include an independent control module.

Furthermore, the controller 1704 and the display 1404 may have the same configurations as the controller 1701 and the display 1401 shown in FIG. 4, respectively. The input unit 1602 and the image processor 1202 may also have the same configurations as the input unit 1601 shown in FIG. 8 and the image processor 1201 shown in FIG. 10, respectively. If the body marker generating apparatus 104 is included in the ultrasound imaging apparatus (100 of FIG. 2), the body marker generating apparatus 104 may further include the ultrasound transceiver 1100, the communication module 1300, and the memory 1500, shown in FIG. 2, as well as the controller 1704, the display 1404, the input unit 1602, and the image processor 1202.

Since the display 1404 performs the same operations as described above with reference to FIGS. 1 through 12, a detailed description of the display 1404 is omitted.

The image processor 1202 segments a shape of the object 10 in a medical image. For example, to do so, the image processor 1202 may detect contours of the object 10 from the medical image and connect the detected contours. Since the image processor 1202 performs the same operations as described with reference to FIGS. 10 and 11A and 11B, a detailed description thereof is omitted.

The controller 1704 selects a first body marker based on the shape of the object 10 segmented by the image processor 1202. For example, the controller 1704 may determine a body marker that is the most similar to the shape of the object 10 as the first body marker, from among a plurality of body markers stored in the body marker generating apparatus 104. Then, the display 1404 may output a first body marker selected by the controller 1704 to a screen. In this case, the first body marker may include a 2D or 3D body marker.

Thereafter, the input unit 1602 receives a user input for designating one from among a plurality of prestored body markers. For example, a user may select a body marker other than the first body marker output to the display 1404. Then, the controller 1704 replaces the first body marker with the other body marker selected by the user based on the user input received from the input unit 1602. An example where the controller 1704 changes a first body marker will now be described in detail with reference to FIGS. 13A through 13D.

FIGS. 13A through 13D are diagrams for explaining an example of replacement of a first body marker performed by the controller 1704, according to an exemplary embodiment.

Figure 13A:
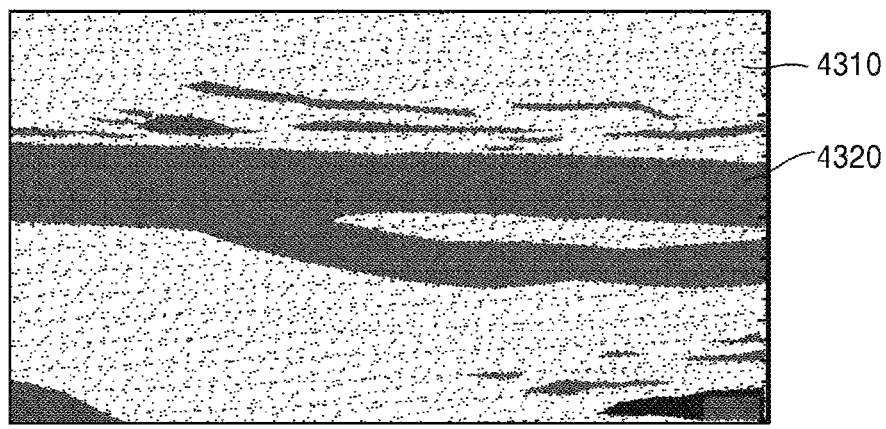
FIGS. 13A through 13D show an example of change of a first body marker by a controller according to an exemplary embodiment.

FIG. 13A illustrates a medical image 4310 showing a blood vessel 4320. The image processor 1202 segments a shape of the blood vessel 4320 in the medical image 4310. For example, the image processor 1202 may segment a shape of the blood vessel 4320 in the medical image 4310 by using any one of the segmentation methods described with reference to FIG. 10.

Figure 13B:
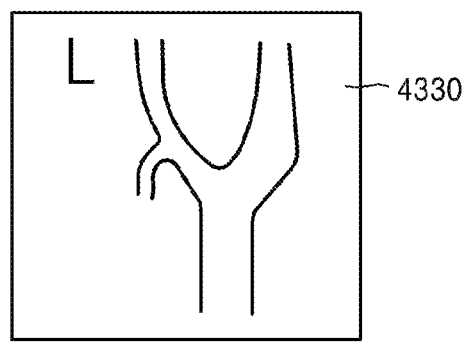

Referring to FIG. 13B, the controller 1704 selects a first body marker 4330 from among a plurality of prestored body markers based on the shape of the blood vessel 4320. For example, the controller 1704 may select a body marker that is the most similar to the shape of the blood vessel 4320 as the first body marker 4330.

The first body marker 4330 selected by the controller 1704 may not contain accurate information about the blood vessel 4320. For example, if the blood vessel 4320 is a right coronary artery, the controller 1704 may select a body marker representing a left coronary artery that is similar to the right coronary artery as the first body marker 4330. In other words, the first body marker 4330 may need to be replaced with another body marker.

Figure 13C:
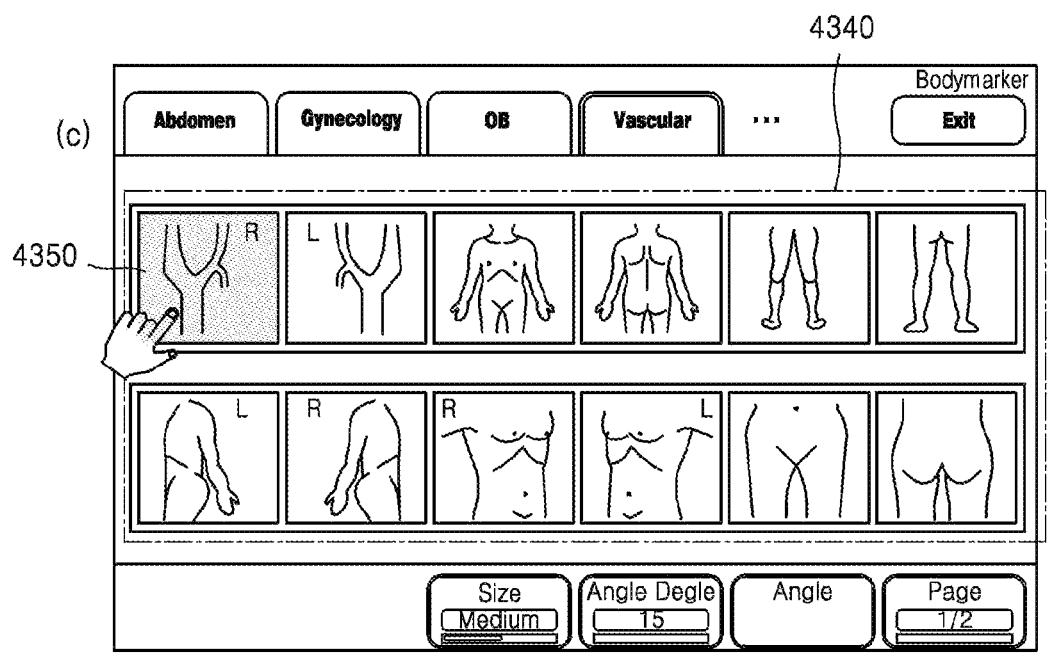

Referring to FIG. 13C, the input unit 1602 receives a user input for designating a body marker 4350 from among a plurality of body markers 4340. For example, if the display 1404 outputs the first body marker 4330 to a screen, the user may determine if the first body marker 4330 corresponds to the blood vessel 4320 shown in the medical image 4310. If the first body marker 4330 does not correspond to the blood vessel 4320, the user may designate the body marker 4350 corresponding to the blood vessel 4320 from among the plurality of body markers 4340. Since the user may designate the body marker 4350 via the input unit 1602 in the same manner as described above with reference to FIG. 8 and FIGS. 9A and 9B, a detailed description thereof is omitted.

Figure 13D:
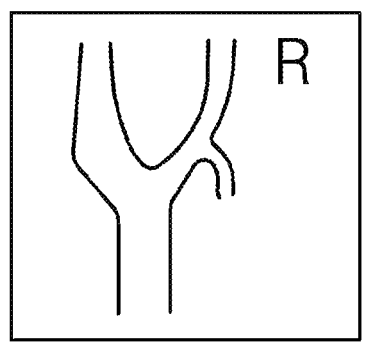

Referring to FIG. 13D, the controller 1704 may change the first body marker 4330 to the body marker 4350 designated by the user. Thus, the body marker 4350 may be determined as a new first body marker.

FIGS. 13E through 13H are diagrams for explaining an example of change of a first body marker by the controller 1704, according to another exemplary embodiment.

Figure 13E:
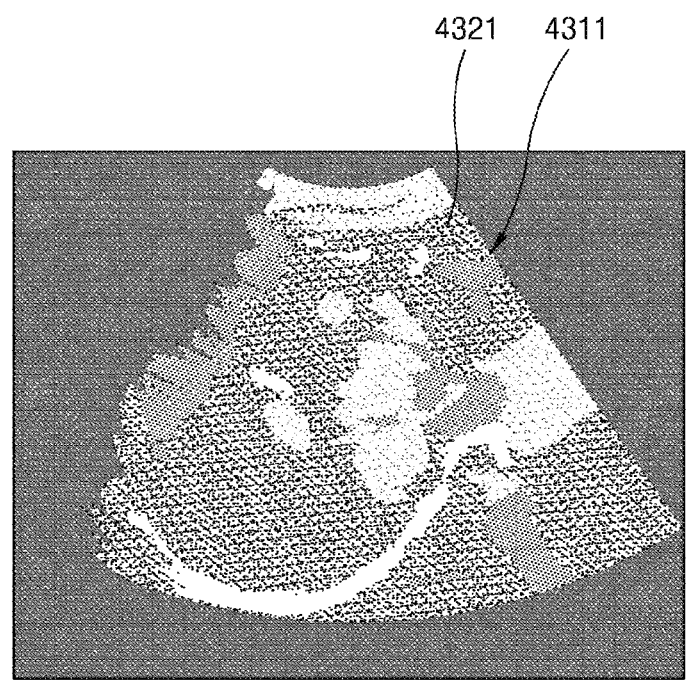
FIGS. 13E through 13H show an example of change of a first body marker by a controller according to another exemplary embodiment.

FIG. 13E illustrates a medical image 4311 showing a liver 4321. The image processor 1202 segments a shape of the liver 4321 in the medical image 4311. For example, the image processor 1202 may segment a shape of the liver 4321 in the medical image 4311 by using any one of the segmentation methods described with reference to FIG. 10.

Figure 13F:
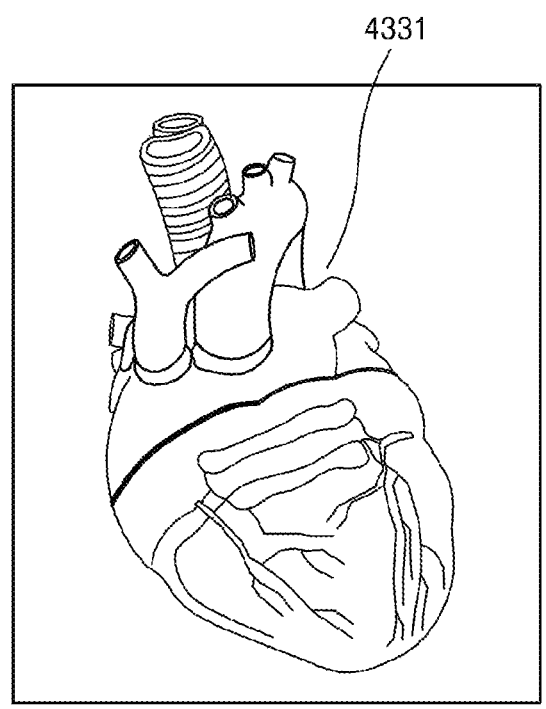

Referring to FIG. 13F, the controller 1704 selects a first body marker 4331 from among a plurality of prestored body markers based on the shape of the liver 4321. In this case, the first body marker 4331 may be a body marker having a 3D shape. In addition, the first body marker 4331 selected by the controller 1704 may not be a body marker depicting the liver 4321.

Figure 13G:
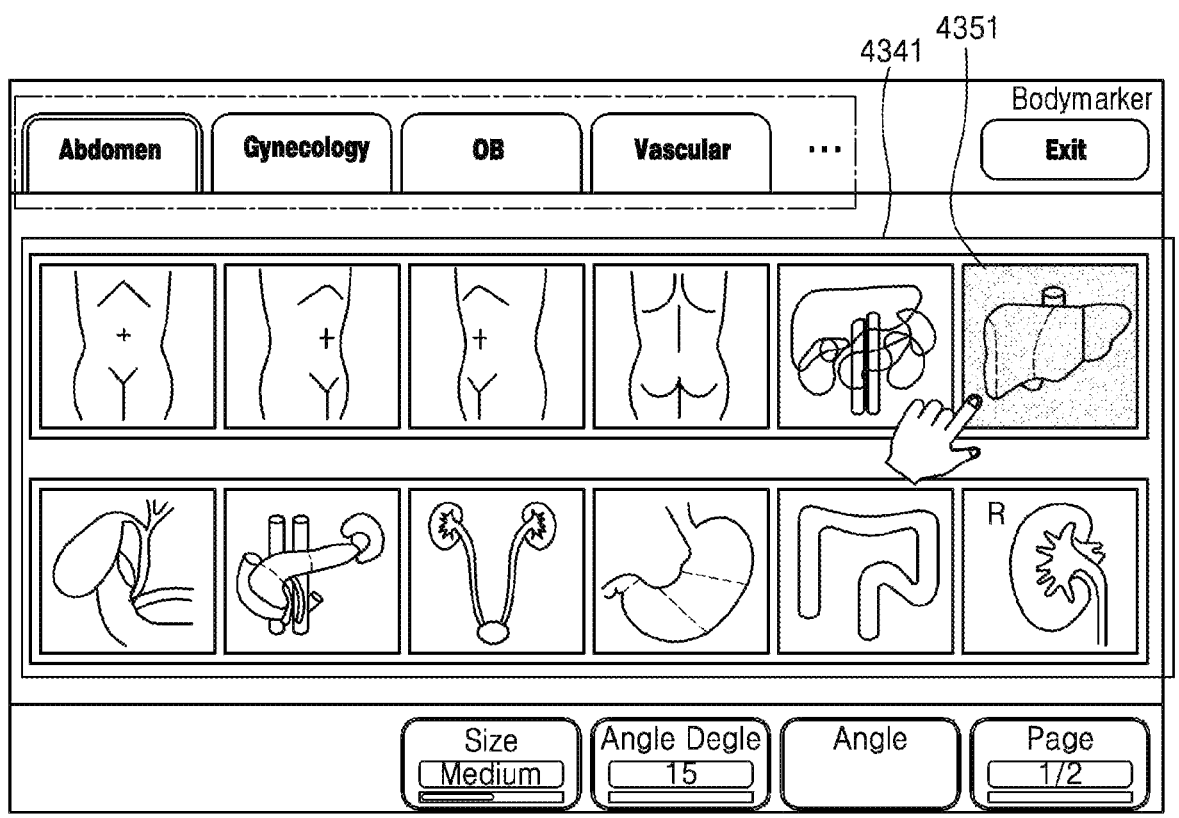

Referring to FIG. 13G, the input unit 1602 receives a user input for designating a body marker 4351 from among a plurality of body markers 4341. For example, if the display 1404 outputs the first body marker 4331 on a screen, the user may determine if the first body marker 4331 corresponds to the liver 4321 shown in the medical image 4311. If the first body marker 4331 does not correspond to the liver 4321, the user may designate the body marker 4351 corresponding to the liver 4321 from among the plurality of body markers 4341.

Figure 13H:
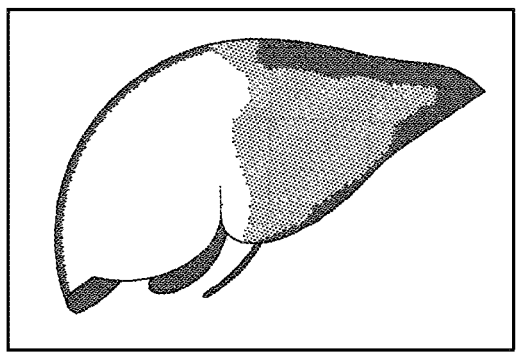

Referring to FIG. 13H, the controller 1704 may change the first body marker 4331 to the body marker 4351 designated by the user. Thus, the body marker 4351 may be determined as a new first body marker. In this case, the body marker 4351 may be output as a body marker having a 3D shape.

After a first body marker is determined according to the method described above with reference to FIGS. 8 through 13H, the controller 1704 generates a second body marker by using the first body marker. In detail, the controller 1704 may generate a second body marker in which a portion of the first body marker corresponding to an object has been emphasized. Examples where the controller 1704 generates a second body marker will now be described with reference to FIGS. 14A through 14C and 15A through 15C.

FIGS. 14A through 15C are diagrams for explaining an example of generation of a second body marker performed by the controller 1704 according to an exemplary embodiment.

To generate a second body marker, the controller 1704 may partition a first body marker into a plurality of portions. For example, the controller 1704 may partition the first body marker into a plurality of portions based on a user input. In this case, the user input means a signal that is input by the user for partitioning the first body marker. The signal may be input by selecting (e.g., by clicking or tapping) a predetermined button displayed on a screen. The user input may be received via the input unit 1602.

For example, if the first body marker is a 2D body marker, the controller 1704 may partition the first body marker into a plurality of portions that include a portion corresponding to a shape of an object shown in a medical image. For example, if an organ corresponding to the first body marker is the liver and an object in the medical image is a left lobe, the controller 1704 may partition the first body marker into a plurality of portions that include a portion corresponding to the left robe.

As another example, if the first body marker is a 3D body marker, the controller 1704 may partition the first body marker according to prestored anatomical theory. In this case, partitioning the first body marker according to the prestored anatomical theory means dividing an organ corresponding to the first body marker according to detailed configurations of the organ. For example, if an organ corresponding to the first body marker is the liver, the controller 1704 may partition the liver into a left robe, a right robe, gallbladder, diaphragm, a hepatic vein, a hepatic portal vein, inferior vena cava, falciform ligament, etc., according to the anatomical features of the liver.

The controller 1704 may also generate a second body marker including some of the plurality of portions that have been emphasized to distinguish them from the remaining portions. Some of the plurality of portions have been emphasized to distinctly indicate them as a line having a different thickness than that of a line representing the remaining portions thereof or as a color that is different from that representing the remaining portions. Alternatively, some of the plurality of portions have been emphasized to distinctly indicate them in a different size than the remaining portions.

For example, the controller 1704 may generate a second body marker including some of the plurality of portions that have been emphasized to distinguish them from the remaining portions based on a user input. In this case, the user input means a signal that is input by the user for selecting at least one of the plurality of portions. The signal may be input by selecting (e.g., by clicking or tapping) one of the plurality of portions displayed on a screen. The user input may be received via the input unit 1602.

As another example, the controller 1704 may generate a second body marker including some of the plurality of portions that have been emphasized to distinguish them from the remaining portions based on a shape of an object in a medical image. In other words, the controller 1704 may generate a second body marker in which a portion including a shape of an object in a medical image has been emphasized.

An example where the controller 1704 generates a second body marker by partitioning a first body marker into a plurality of portions and emphasizing one of the plurality of portions will be described in more detail below with reference to FIGS. 15D through 15F.

Figure 14A:
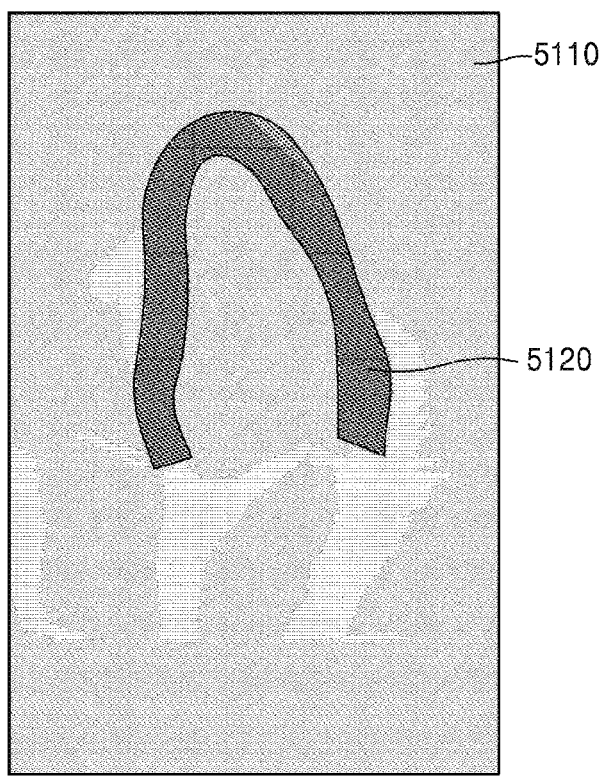
FIGS. 14A through 14C are diagrams for explaining an example of generation of a second body marker by a controller according to an exemplary embodiment.

FIG. 14A illustrates a medical image 5110 showing an object 5120. If the object 5120 is a portion of the heart, the controller 1704 accurately identifies which portion of the heart corresponds to the object 5120. For example, if the medical image 5110 is obtained by capturing a left atrium of the heart, the controller 1704 determines that the object 5120 is the left atrium of the heart. In this case, the controller 1704 may determine that the object 5120 is the left atrium of the heart based on a shape of the object 5120 segmented by the image processor 1202.

Figure 14B:
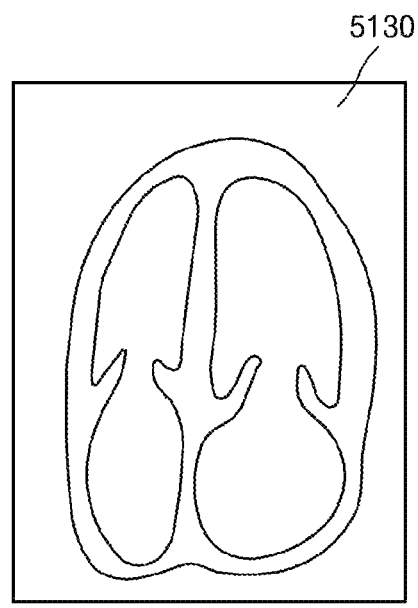
Figure 14C:
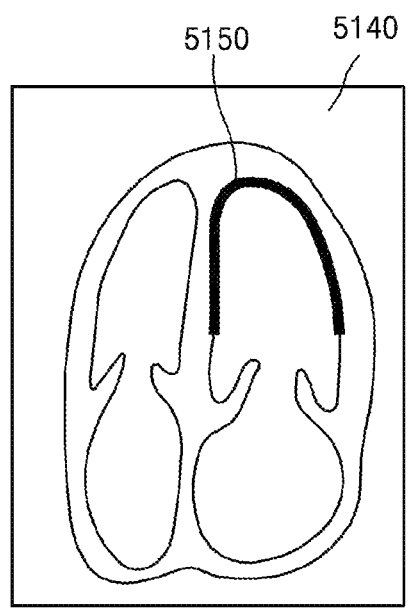

Referring to FIGS. 14B and 14C, the controller 1704 retrieves a portion 5150 corresponding to the object 5120 from a first body marker 5130. The controller 1704 may then indicate the portion 5150 as a line that is thicker or thinner than a line depicting the first body marker 5130. Alternatively, the controller 1704 may indicate the portion 5150 as a different type of line than a line depicting the remaining portions. For example, if the first body marker 5130 is indicated by a solid line, the controller 1704 may indicate the portion 5150 as a broken line.

The controller 1704 may generate a second body marker 5140 by processing the first body marker 5130 in such a manner as described above.

Figure 15A:
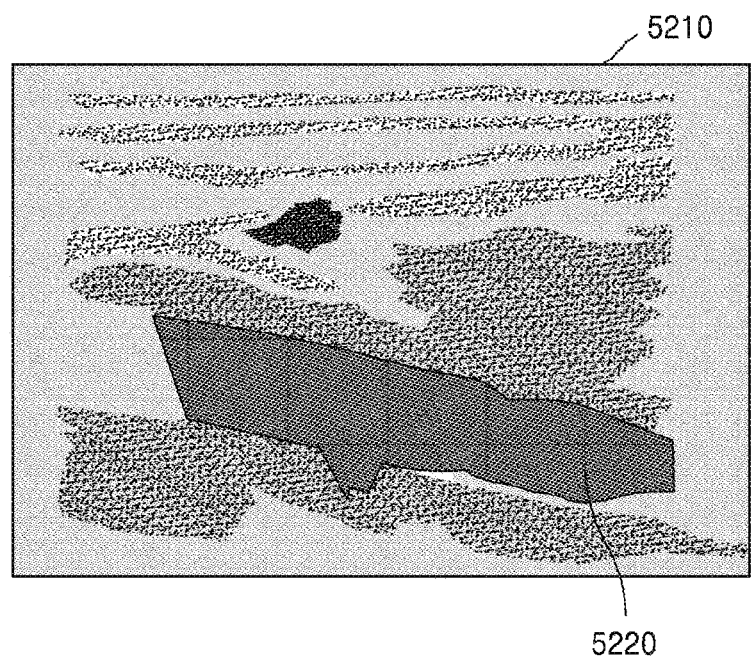
FIGS. 15A through 15C are diagrams for explaining an example of generation of a second body marker by a controller according to another exemplary embodiment.
Figure 15B:
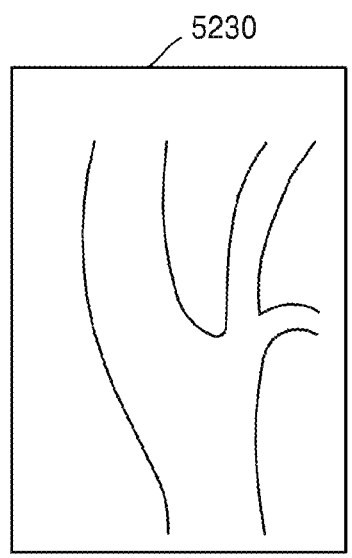
Figure 15C:
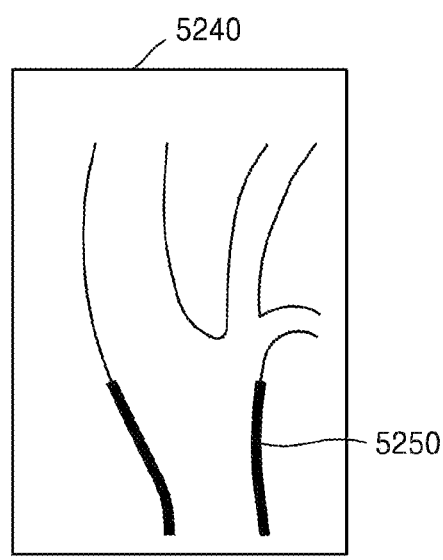

FIGS. 15A through 15C are diagrams for explaining an example of generation of a second body marker performed by the controller 1704 according to another exemplary embodiment FIG. 15A illustrates a medical image 5210 showing an object 5220. If the object 5220 is a portion of a blood vessel, the controller 1704 accurately identifies which portion of the blood vessel corresponds to the object 5220. For example, if the medical image 5210 is obtained by capturing a coronary artery, the controller 1704 determines that the object 5220 is the coronary artery. In this case, the controller 1704 may determine that the object 5220 is the coronary artery based on a shape of the object 5220 segmented by the image processor 1202.

Referring to FIGS. 15B and 15C, the controller 1704 retrieves a portion 5250 corresponding to the object 5220 from a first body marker 5230. The controller 1704 may then indicate the portion 5250 as a line having a different color from that representing the remaining portions of the first body marker 5230. For example, if the first body marker 5230 is indicated as a white line, the controller 1704 may indicate the portion 5250 as a red line.

The controller 1704 may generate a second body marker 5240 by processing the first body marker 5230 in such a manner as described above.

Figure 15D:
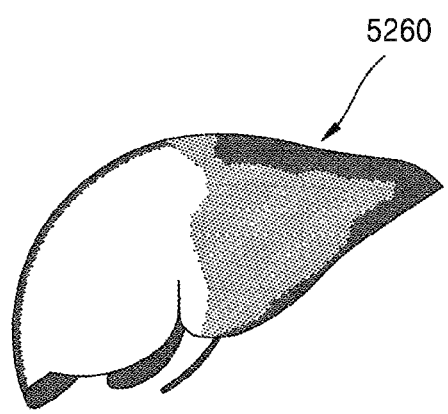
FIGS. 15D through 15F are diagrams for explaining an example of generation of a second body marker by a controller according to another exemplary embodiment.
Figure 15E:
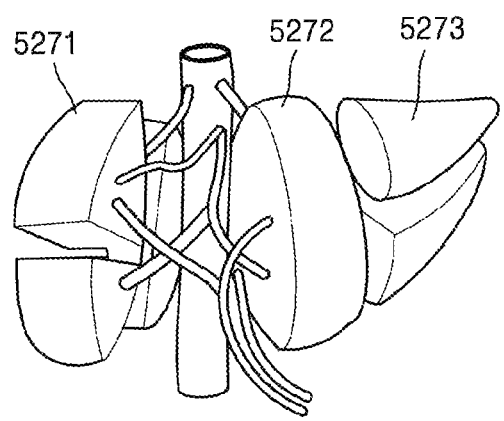
Figure 15F:
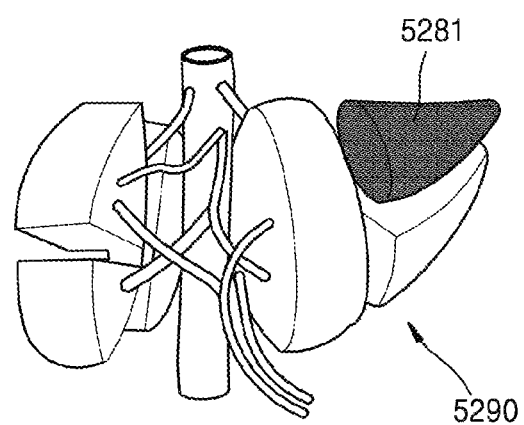

FIGS. 15D through 15F are diagrams for explaining an example of generation of a second body marker by the controller 1704 according to another exemplary embodiment.

FIG. 15D illustrates a first body marker 5260. For convenience of explanation, it is assumed that the first body marker 5260 in FIGS. 15D through 15F is a 3D body marker representing a liver.

Referring to FIG. 15E, the controller 1704 partitions the first body marker 5260 into a plurality of portions. For example, the controller 1704 may partition the liver shown in the first body marker 5260 into a plurality of structural portions 5271 through 5273.

Referring to FIG. 15F, the controller 1704 may generate a second body marker 5290 including one of the plurality of structural portions 5271 through 5273 that has been emphasized to distinguish it from the remaining portions. In this case, an emphasized portion 5281 of the second body marker 5290 may be a portion selected by a user from among the plurality of structural portions 5271 through 5273 displayed on a screen or be automatically selected by the controller 1704 based on a shape of an object in a medical image. In this case, if the user determines that the portion selected by the controller 1704 is different from the object in the medical image, the user may select another portion from among the plurality of structural portions 5271 through 5273.

For example, the emphasized portion 5281 of the second body marker 5290 may be indicated by a line having a different thickness than that of a line depicting the remaining portions or by a color that is different from that representing the remaining portions.

Figure 16:
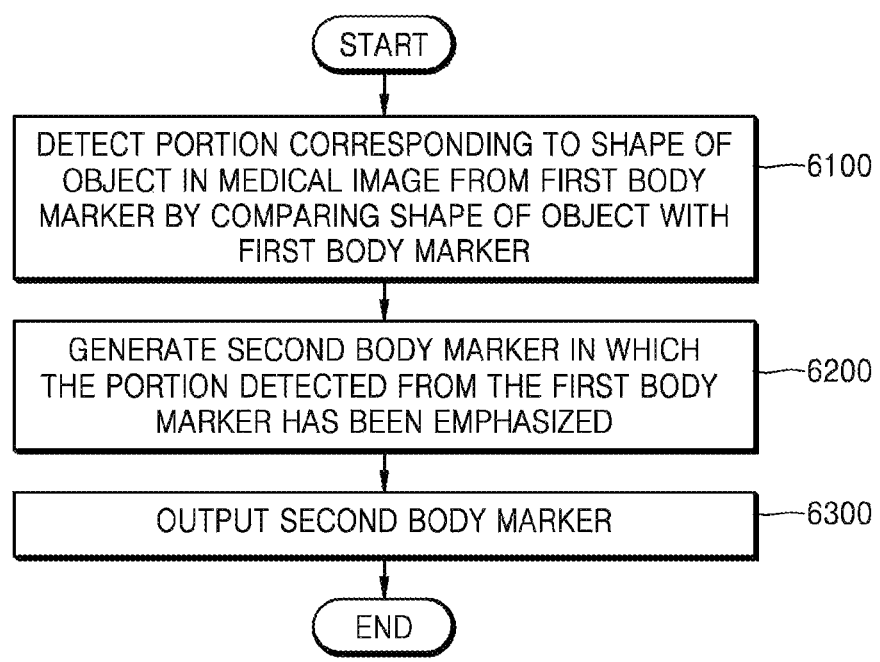
FIG. 16 is a flowchart of a method of generating a body marker according to an exemplary embodiment.

FIG. 16 is a flowchart of a method of generating a body marker according to an exemplary embodiment.

Referring to FIG. 16, the method of generating a body marker includes operations sequentially processed by the ultrasound diagnosis system 1000 of FIG. 1A (1001 of FIG. 1B or 1002 of FIG. 2) or the body marker generating apparatus 101 of FIG. 4 (102 of FIG. 8, 103 of FIG. 10, or 104 of FIG. 12). Thus, although omitted hereinafter, descriptions of the ultrasound diagnosis systems 1000 of FIG. 1A, 1001 of FIG. 1B, and 1002 of FIG. 2 or the body marker generating apparatuses 101 of FIG. 4, 102 of FIG. 8, 103 of FIG. 10, and 104 of FIG. 12 are also applied to the method of FIG. 16.

A controller detects a portion corresponding to a shape of an object shown in a medical image from a first body marker by comparing the shape of the object with the first body marker (operation 6100). In this case, the first body marker may be one selected from among a plurality of body markers prestored in a memory. For example, the controller may select the first body marker based on a user input. As another example, the controller may select the first body marker based on a shape of the object segmented by an image processor from the medical image. As another example, the controller may replace the selected first body marker to another body marker based on a user input. In this case, each of the first and second body markers may include a 2D or 3D body marker.

The controller generates a second body marker in which a portion of the first body marker corresponding to an object has been emphasized (operation 6200). For example, the controller may detect the portion corresponding to the shape of the object from the first body marker and indicate the detected portion as a line having a different thickness than that of a line depicting the first body marker. As another example, the controller may detect a portion corresponding to the shape of the object from the first body marker and indicate the detected portion as a color that is different from a color representing the first body marker. Furthermore, the controller may partition the first body marker into a plurality of portions and generate a second body marker including some of the plurality of portions that have been emphasized.

A display outputs the second body marker (operation 6300). In this case, the display may output the first and second body markers together to a single screen.

As described above, according to the one or more of the above exemplary embodiments, a body marker generating apparatus may generate a second body marker that accurately indicates a position of an object shown in a medical image. Thus, by referring to the second body marker, a viewer who sees the medical image may obtain accurate information about the type of the object and a current position thereof.

The methods of generating a body marker according to the exemplary embodiments can be recorded as programs that can be executed on a computer and be implemented through general-purpose digital computers which can run the programs using a computer-readable recording medium. Data structures described in the above methods can also be recorded on a computer-readable recording medium in a variety of ways. Examples of the computer-readable recording medium include storage media such as magnetic storage media (e.g., ROM, RAM, Universal Serial Bus (USB), floppy disks, hard disks, etc.) and optical recording media (e.g., CD-ROMs or DVDs).

While one or more exemplary embodiments have been described with reference to the figures, it will be understood by one of ordinary skill in the art that various changes in form and details may be made therein without departing from the spirit and scope of the present inventive concept as defined by the following claims. Thus, it should be understood that the exemplary embodiments described therein should be considered in a descriptive sense only and not for purposes of limitation. The scope of the inventive concept is defined not by the detailed description thereof but by the appended claims, and all differences within the scope of the appended claims and their equivalents will be construed as being included in the present inventive concept.

What is claimed is:

1. A method of generating a body marker, the method comprising:
   displaying a medical image showing a region of an object;
   displaying a list of a plurality of prestored body markers which represent different types of organs of a human body;
   receiving a user input for designating one body marker which represents a type of an organ from among the plurality of prestored body markers;
   selecting the designated body marker as a first body marker based on the user input;
   partitioning the first body marker into a plurality of portions according to a predetermined segmentation rule with respect to the type of the organ corresponding to the first body marker;
   generating a second body marker by emphasizing a portion corresponding to the region shown in the medical image from among the plurality of portions of the first body marker so that the portion is distinguishable from other portions; and
   displaying the second body marker with the medical image.

2. The method of claim 1, wherein each of the first and second body markers comprises a two-dimensional (2D) or three-dimensional (3D) body marker.

3. The method of claim 1, further comprising:
   receiving another user input for designating another body marker from among the plurality of prestored body markers; and
   changing the first body marker based on the other user input.

4. The method of claim 1, wherein, in the generating of the second body marker, the second body marker is generated by emphasizing the portion corresponding to the region shown in the medical image with a line having a different thickness than that of a line depicting the other portions of the first body marker.

5. The method of claim 1, wherein, in the generating of the second body marker, the second body marker is generated by emphasizing the portion corresponding to the region shown in the medical image with a color that is different from a color representing the other portions of the first body marker.

6. The method of claim 1, wherein, in the generating of the second body marker, the second body marker is generated by emphasizing the portion corresponding to the region shown in the medical image as being larger than the other portions of the first body marker.

7. The method of claim 1, wherein the medical image comprises one selected from the group consisting of an amplitude (A) mode ultrasound image, a brightness (B) mode ultrasound image, a motion (M) mode ultrasound image, and a Doppler mode ultrasound image.

8. A non-transitory computer-readable having recorded thereon a program, which when executed by a computer, performs the method of claim 1.

9. An apparatus for generating a body marker, the apparatus comprising:
   a display configured to:
      display a medical image showing a region of an object, and
      display a list of a plurality of prestored body markers which represent different types of organs of a human body;
   an input unit configured to receive a user input for designating one body marker which represents a type of an organ from among the plurality of prestored body markers; and
   a controller configured to:
      select the designated body marker as a first body marker based on the user input,
      partition the first body marker into a plurality of portions according to a predetermined segmentation rule with respect to the type of the organ corresponding to the first body marker, and
      generate a second body marker by emphasizing a portion corresponding to the region shown in the medical image from among the plurality of portions of the first body marker so that the portion is distinguishable from other portions,
   wherein the display is further configured to display the second body marker with the medical image.

10. The apparatus of claim 9, wherein each of the first and second body markers comprises a two-dimensional (2D) or three-dimensional (3D) body marker.

11. The apparatus of claim 9, wherein the input unit is further configured to receive another user input for designating another body marker from among the plurality of prestored body markers;
   wherein the controller is further configured to change the first body marker based on the user input.

12. The apparatus of claim 9, wherein the controller is further configured to generate the second body marker by emphasizing the portion corresponding to the region shown in the medical image with a line having a different thickness than that of a line depicting the other portions of the first body marker.

13. The apparatus of claim 9, wherein the controller is further configured to generate the second body marker by emphasizing the portion corresponding to the region shown in the medical image with a color that is different from a color representing the first body marker.

14. The apparatus of claim 9, wherein the controller is further configured to generate the second body marker by emphasizing the portion corresponding to the region shown in the medical image as being larger than the other portions of the first body marker.

15. The apparatus of claim 9, wherein the medical image comprises one selected from the group consisting of an amplitude (A) mode ultrasound image, a brightness (B) mode ultrasound image, a motion (M) mode ultrasound image, and a Doppler mode ultrasound image.

\* \* \* \* \*